(12) United States Patent
De Lucca et al.

(10) Patent No.: US 8,952,219 B2
(45) Date of Patent: Feb. 10, 2015

(54) **METHODS FOR *AGROBACTERIUM*-MEDIATED TRANSFORMATION OF SUGAR CANE**

(75) Inventors: Paulo Cezar De Lucca, Campinas (BR); Shujie Dong, Cary, NC (US); Robert Jason Christopher Geijskes, Brisbane (AU); Erik Martin Dunder, Hillsborough, NC (US); Manuel Benito Sainz, Ribeirao Preto (BR)

(73) Assignees: Syngenta Participations AG, Basel (CH); Queensland University of Technology, Brisbane (AU)

(*) Notice: Subject to any disclaimer, the term of this patent is extended or adjusted under 35 U.S.C. 154(b) by 527 days.

(21) Appl. No.: 13/378,497

(22) PCT Filed: Jun. 24, 2010

(86) PCT No.: PCT/US2010/039774
§ 371 (c)(1),
(2), (4) Date: Mar. 2, 2012

(87) PCT Pub. No.: WO2010/151634
PCT Pub. Date: Dec. 29, 2010

(65) Prior Publication Data
US 2012/0156673 A1 Jun. 21, 2012

Related U.S. Application Data

(60) Provisional application No. 61/220,405, filed on Jun. 25, 2009, provisional application No. 61/290,803, filed on Dec. 29, 2009.

(51) Int. Cl.
*A01H 1/02* (2006.01)
*C12N 15/82* (2006.01)

(52) U.S. Cl.
CPC .................. *C12N 15/8205* (2013.01)
USPC .................. 800/294; 800/268; 800/279

(58) Field of Classification Search
None
See application file for complete search history.

(56) References Cited

U.S. PATENT DOCUMENTS

| | | | |
|---|---|---|---|
| 5,563,055 | A | 10/1996 | Townsend et al. |
| 5,981,840 | A | 11/1999 | Zhao et al. |
| 7,045,357 | B2 | 5/2006 | Cheng et al. |
| 2001/0054186 | A1 | 12/2001 | Cheng et al. |
| 2004/0237133 | A1 | 11/2004 | Goldman et al. |
| 2006/0130175 | A1 | 6/2006 | Ellis et al. |
| 2008/0118981 | A1 | 5/2008 | Akula et al. |
| 2008/0118987 | A1 | 5/2008 | Eastwood et al. |

FOREIGN PATENT DOCUMENTS

| | | |
|---|---|---|
| WO | WO 00/34491 A2 | 6/2000 |
| WO | WO 0237951 A1 * | 5/2002 |

OTHER PUBLICATIONS

Cheng et al. ( In Vitro Cell. Dev. Biol. Plant, (2003), 39: pp. 595-604).*
Snyman et al. (Plant Cell Rep., (2006), 25: pp. 1016-1023).*
Saharan et al. (African Journal of Biotechnology, vol. 3 (5), pp. 256-259, (2004)).*
Extended European Search Report in corresponding European Patent Application No. 1079642.0, mailed Nov. 21, 2013 (6 pages).
Cheng M. et al., "Factors Influencing *Agrobacterium* -Mediated Transformation of Monocotyledonous Species", *In Vitro Cell. Dev. Biol.—Plant*, 40:31-45, Jan.-Feb. 2004.
Arencibia A.D. et al., "An efficient protocol for sugarcane (*Saccharum* spp. L.) transformation mediated by *Agrobacterium tumefaciens*", *Transgenic Research*, vol. 7 (1998), pp. 231-222.
Arencibia A.D. et al., "Sugarcane (*Saccharum* spp.)", *Methods in Molecular Biology*, vol. 344, *Agrobacterium Protocols, 2/e* vol. 2, ed. Wang ($2^{nd}$ ed., Humana Press, Inc.), 2007, pp. 227-235.
Cheng M. et al., "Desiccation of Plant Tissues Post-*Agrobacterium*Infection Enhances T-DNA Delivery and Increases Stable Transformation Efficiency in Wheat", *In Vitro Cell. Dev. Biol.—Plant*, Nov.-Dec. 2003, vol. 39, pp. 595-604.
de la Riva G.A. et al., "*Agrobacterium tumefaciens* : a natural tool for plant transformation", *Electronic Journal of Biotechnology*, vol. 1, No. 3, Dec. 15, 1998, pp. 118-133.
Lakshmanan P. et al., "Invited Review: Sugarcane Biotechnology: The Challenges and Opportunities", *In Vitro Cell. Dev. Biol.—Plant*, Jul.-Aug. 2005, vol. 41, pp. 345-363.
Manickavasagam M. et al., "*Agrobacterium*-mediated genetic transformation and development of herbicide-resistant sugarcane (*Saccharum* species hybrids) using axillary buds", *Plant Cell Rep*, (2004), vol. 23, pp. 134-143.

(Continued)

*Primary Examiner* — Brent T Page
*Assistant Examiner* — Jared Shapiro
(74) *Attorney, Agent, or Firm* — Myers Bigel Sibley & Sajovec, PA

(57) ABSTRACT

The present invention provides methods for producing a transformed sugar cane tissue or cell thereof, said methods comprising: a) inoculating a sugar cane tissue or a cell thereof with an *Agrobacterium* inoculation suspension, said *Agrobacterium* comprising a nucleic acid of interest, to obtain an *Agrobacterium*-inoculated sugar cane tissue or cell thereof; b) co-cultivating said *Agrobacterium*-inoculated sugar cane tissue or cell thereof on a surface in the absence of co-culture media for a time period sufficient to reduce original weight of said *Agrobacterium*-inoculated sugar cane tissue or cell thereof; and c) selecting a transformed sugar cane tissue or a cell thereof comprising said nucleic acid of interest. The transformation methods of the invention provide for increased transformation frequency and recovery of transgenic sugar cane plants.

14 Claims, No Drawings

(56) References Cited

OTHER PUBLICATIONS

Opabode J.T. et al., "*Agrobacterium*-mediated transformation of plants: emerging factors that influence efficiency", *Biotechnology and Molecular Biology Review*, vol. 1 (1), Apr. 2006, pp. 12-20.

Vogel J. et al., "High-efficiency *Agrobacterium*-mediated transformation of *Brachypodium distachyon* inbred line Bd21-3", *Plant Cell Rep* (2008), 27:471-478.

Zhang S.Z. et al., "Expression of the *Grifola frondosa* Trehalose Synthase Gene and Improvement of Drought-Tolerance in Sugarcane (*Saccharum officinarum* L.)", *Journal of Integrative Plant Biology*, 2006, vol. 48, No. 4, pp. 453-459.

International Search Report and Written Opinion of International Application. No. PCT/US2010/039774, mailed Aug. 27, 2010 (10 pages).

Gonzalez et al., Efficient regeneration and *Agrobacterium tumefaciens* mediated transformation of recalcitrant sweet potato (*Ipomoea batatas* L.) cultivars., *Asia Pacific J. Mol. Biol. Biotechnol.* 16(2):25-33 (2008).

Patel et al., "Enhancing *Agrobacterium tumefaciens*-mediated transformation efficiency of perennial ryegrass and rice using heat and high maltose treatments during bacterial infection", Plant Cell Tiss. Organ Cult. 114:19-29 (2013).

\* cited by examiner

METHODS FOR *AGROBACTERIUM*-MEDIATED TRANSFORMATION OF SUGAR CANE

STATEMENT OF PRIORITY

This application is a 35 U.S.C. §371 national phase application of International Application Serial No. PCT/US2010/039774, filed Jun. 24, 2010, which claims the benefit, under 35 U.S.C. §119 (e), of U.S. Provisional Application No. 61/220,405; filed Jun. 25, 2009, and of U.S. Provisional Application No. 61/290,803; filed Dec. 29, 2009, the entire contents of each of which are incorporated by reference herein.

FIELD OF THE INVENTION

The invention relates generally to plant molecular biology, particularly methods for *Agrobacterium*-mediated transformation of sugar cane.

BACKGROUND

Sugar cane (*Saccharum* spp.) is an important source of raw material for sugar industries and for allied industries involved in the production of such products as alcohol, acetic acid, butanol, paper, plywood, industrial enzymes, and animal feed. These industries seek to improve sugar cane by introducing heterologous polynucleotides that confer desirable characteristics or traits.

*Agrobacterium tumefaciens* is a soil-borne pathogen that is widely used to introduce heterologous polynucleotides into plant cells, including plant cells from sugar cane. *A. tumefaciens* transfers a particular polynucleotide segment of a tumor-inducing (Ti) plasmid into the nucleus of infected host cells, which subsequently stably integrates into the host's genome. Advantageously, heterologous polynucleotides can be placed between the borders of the Ti plasmid and transferred to plant cells.

Although *Agrobacterium*-mediated transformation has been used for genetic manipulation of sugar cane, efficiency and reproducibility of the available methodologies continue to be a challenge. In fact, *A. tumefaciens* induces necrosis in cultured, transformed sugar cane tissue, with a resultant low transformation frequency (Arencibia et al. (1998) *Transgenic Res.* 7:123-222; Enriquez-Obregón et al. (1997) *Biotecnologia Aplicada* 14:169-174; and de la Riva et al. (1998) *Electron. J. Biotechno.* 1:118-133).

Because of the importance of manipulating sugar cane for improved characteristics (e.g., increased resistance to biotic or abiotic stresses, or improved production), there is a need for additional methods that advantageously increase the efficiency of *Agrobacterium*-mediated transformation of this important agricultural crop.

Accordingly, the present invention overcomes the deficiencies in the art by providing methods of *Agrobacterium*-mediated transformation of sugar cane and other important plants that result in greater transformation efficiencies.

SUMMARY OF THE INVENTION

Methods for *Agrobacterium*-mediated transformation of sugar cane (*Saccharum* spp.) are provided. The methods comprise a protocol, wherein *Agrobacterium*-inoculated sugar cane tissues are co-cultivated under a desiccating or an extreme desiccating environment prior to selection of transformed tissue. Treatments can be designed that induce prolonged desiccation of varying severity. The transformation methods of the invention provide for increased transformation frequency and recovery of transgenic sugar cane plants.

Accordingly, the present invention provides producing a transformed sugar cane tissue or cell thereof, said method comprising: a) inoculating a sugar cane tissue or a cell thereof with an *Agrobacterium* inoculation suspension, said *Agrobacterium* comprising a nucleic acid of interest, to obtain an *Agrobacterium*-inoculated sugar cane tissue or cell thereof; and b) co-cultivating said *Agrobacterium*-inoculated sugar cane tissue or cell thereof on a surface in the absence of co-culture media for a time period sufficient to reduce original weight of said *Agrobacterium*-inoculated-inoculated sugar cane tissue or cell thereof; thereby producing a transformed sugar cane tissue or cell thereof.

DETAILED DESCRIPTION OF THE INVENTION

The present invention is directed to *Agrobacterium*-mediated transformation methods comprising a co-cultivation protocol that allows for increased efficiency of transfer of a nucleic acid of interest from the *Agrobacterium* into inoculated sugar cane cells and tissues. The *Agrobacterium*-mediated transformation methods of the present invention comprise co-cultivating an *Agrobacterium*-inoculated sugar cane tissue or cell thereof on a surface in a desiccating environment for a time period sufficient to reduce the original weight of the inoculated tissue prior to selecting transformed cells or transformed tissue. In some embodiments, the desiccating environment can be extreme in that excess bacterial (e.g., *Agrobacterium*) inoculation suspension is removed prior to co-cultivation of the tissue with the bacteria in the absence of co-culture media. Following exposure to this desiccation step, the inoculated plant material or tissue can be subjected to a selection step to identify successful transformation events.

Desiccation of plant parts prior to or during co-cultivation with *Agrobacterium* is known in the art. For example, Vogel & Hill showed an improvement in transformation of *Brachypodium distachyon* after a short desiccation treatment of seven minutes at the onset of co-cultivation (Vogel & Hill (2008) *Plant Cell Rep.* 27:471-478). Arencibia et al. showed slight improvements in *Agrobacterium*-mediated transformation in plant parts from sugar cane by air drying cells under laminar flow for 15-60 minutes prior to inoculation (Arencibia et al. (1998) *Transgenic Res.* 7:123-222; see also, Zhang et al. (2006) *J. Integr. Plant Biol.* 48:453-459). Drying treatments lasting more than 60 minutes, however, produced irreversible damage to the plant parts (Arencibia et al. (1998) supra). Cheng and Fry reported that co-culturing plant parts from corn, rice, soybean or wheat with *Agrobacterium* on a filter paper saturated with varying amounts of sterile water for two to three days reduced plant part weight and increased β-glucuronidase expression (U.S. Pat. No. 7,045,357; and Cheng et al. (2003) *In Vitro Cell. Dev. Biol.* 39:595-604). Reducing plant part weight by more than 35%, however, resulted in plant parts that could not recover from the severe water stress (Cheng et al., supra). In contrast to these earlier reports, the present invention in sugar cane provides a broader range of effective treatments resulting in a more extreme level of desiccation of inoculated plant tissue during co-cultivation.

Without being bound by any particular theory or mechanism of action, subjecting *Agrobacterium*-inoculated sugar cane tissues to desiccation during the co-cultivation period following the initial inoculation step beneficially reduces the cellular necrosis/apoptosis of the inoculated plant tissue that is normally observed after exposure of sugar cane tissues to

*Agrobacterium*, and may increase the *Agrobacterium*-mediated delivery of the nucleic acid of interest into the target sugar cane tissues and/or cells thereof. Further, desiccation during the co-cultivation step advantageously improves subsequent cell survival during the selection/recovery/regeneration steps that typically follow the co-cultivation step. As a result, the *Agrobacterium*-mediated transformation methods of the present invention provide for increased recovery of transgenic sugar cane plants.

It is noted that the method of the invention can be applied to any genotype of sugar cane and represents a significant improvement in the transformation arts for sugar cane. There has been a long felt need in the transformation arts for a method of transformation of sugar cane which is not genotype dependent and the present method provides a solution to this problem (See, e.g., Joyce et al. *Plant Cell Rep* 29:173-183 (2009)). The incorporation of desiccation during co-cultivation for *Agrobacterium*-mediated transformation of sugar cane (e.g., *Agrobacterium*-mediated transformation) renders this crop plant less recalcitrant to *Agrobacterium*-mediated transformation (e.g., *Agrobacterium*-mediated transformation).

Accordingly, in some embodiments, the present invention provides methods method of producing a transformed sugar cane tissue or cell thereof, said method comprising: a) inoculating a sugar cane tissue or a cell thereof with an *Agrobacterium* inoculation suspension, said *Agrobacterium* comprising a nucleic acid of interest, to obtain an *Agrobacterium*-inoculated sugar cane tissue or cell thereof; and b) co-cultivating said *Agrobacterium*-inoculated sugar cane tissue or cell thereof on a surface in the absence of co-culture media for a time period sufficient to reduce original weight of said *Agrobacterium*-inoculated sugar cane tissue or cell thereof; thereby producing a transformed sugar cane tissue or cell thereof.

By "co-cultivation" and "co-cultivating" is intended the time period of culture following inoculation of the plant tissue or cell thereof (e.g., contacting the plant tissue or cell thereof with an *Agrobacterium* strain or other bacteria capable of nucleic acid transfer) up until the time period when the bacteria are removed, inactivated or suppressed. Thus, for example, co-cultivating" can refer to the time period of culture following inoculation of the plant tissue or cell thereof up until the time period when the growth and metabolic activity of the bacteria within the inoculated tissue is suppressed by the addition of compounds (e.g., bacteriocidal or bacteriostatic agents) or through processes that inhibit the growth of the bacteria or a combination thereof. As used herein, "suppress," "suppressed," "suppression," (and grammatical variations thereof) means that the activity (e.g., *Agrobacterium* growth and reproduction) is slowed or halted due to the addition of an agent (e g , inhibitor, antibiotic, and the like) and/or a change in the culture (growing) conditions (e.g., media, temperature, humidity, light, and the like) as compared to the activity in the absence of the agent or change. Usually the co-cultivation process ends at the start of a resting, selection or regeneration step.

As used herein, "desiccating environment" means that the co-cultivation step is performed in the absence of semi-solid or liquid co-culture medium thereby allowing the plant tissue being co-cultivated with the *Agrobacterium* to dry, and thus be reduced in its original weight as described below. In other embodiments, "desiccating environment" means co-cultivating the *Agrobacterium*-inoculated plant tissue on a surface without (i.e., in the absence of) co-cultivating media or other added liquid for a time period sufficient to reduce the original weight of the *Agrobacterium*-inoculated plant tissue. As used herein, "co-culture medium" or "co-cultivating medium" and the like, means any medium known in the art for culturing a plant tissue or a cell thereof after inoculation with *Agrobacterium*. The constituents of co-cultivation media are generally known in the art, and include the sugar cane co-culture medium referred to herein as SCCoCult.

In other embodiments of the invention, the *Agrobacterium*-inoculated tissue or cell thereof is subjected to a co-cultivation step that includes culturing the inoculated plant tissue or cell thereof on a surface in an extreme desiccating environment for a time period sufficient to reduce the original weight of the inoculated plant tissue or cell thereof. As used herein, the term "extreme desiccating environment" means excess inoculation suspension is substantially removed prior to the co-cultivation step wherein the tissue is co-cultivated with *Agrobacterium* in the absence of co-cultivation media. In other embodiments, pre-cultivation media is substantially removed prior to the co-cultivation step wherein the tissue or cell thereof is co-cultivated with *Agrobacterium* in the absence of co-cultivation media. Thus, it is recognized that the plant tissue or cell thereof when removed from the inoculation suspension (e.g., a bacterial suspension culture) may retain residual inoculation suspension adhering thereto or the plant tissue or cell thereof when removed from the pre-culture media (e.g., media for the initiation of callus) may retain residual pre-culture media adhering thereto. Therefore, to maximize the desiccating environment of the surface (i.e., create an extreme desiccating environment) that will support the inoculated plant tissue or cell thereof during the co-cultivation step, residual or excess inoculation suspension and/or pre-culture media can be substantially removed from the plant tissue or cell thereof. By "substantially removed" is intended a de minimus or reduced amount of inoculation suspension and/or pre-culture media may be present on (i.e., adhered to) the inoculated plant tissue or cell thereof when it is placed on a surface in a desiccating environment so long as the amount that remains does not counter the objective of the desiccating or extreme desiccating environment (e.g., to reduce the original weight of the inoculated plant tissue or cell thereof as described below). Thus, in some embodiments of the present invention, the inoculation suspension is substantially removed from said *Agrobacterium*-inoculated sugar cane tissue or cell thereof prior to co-cultivating in the absence of co-cultivation media.

Thus, in some embodiments, the *Agrobacterium*-inoculated tissue thereof is subjected to pre-drying which comprises substantially removing inoculation suspension from said *Agrobacterium*-inoculated sugar cane tissue or cell thereof prior to co-cultivating in the absence of co-cultivation media. Any method that substantially removes the *Agrobacterium*-containing inoculation suspension can be used to pre-dry the plant tissue or cell thereof prior to the co-cultivation step. Non-limiting examples of methods for pre-drying include draining, blotting on dry sterile absorbent paper (e.g., filter paper), air drying the inoculated plant tissue, or any combination thereof, prior to the co-cultivation step. Where air drying is used, the inoculated plant tissue can be air dried, for example, under a laminar hood or other means for evaporation, for about 1 minute to about 60 minutes, for example, about 1 minute, about 5 minutes, about 10 minutes, about 15 minutes, about 30 minutes, about 60 minutes, or any time period between about 1 minute and about 60 minutes prior to the co-cultivation step. When blotting with paper, the inoculated plant tissue can be blotted sequentially with multiple sterile papers until the paper shows no signs of wetness or is substantially dry (i.e., a visual inspection of the filter paper immediately after blotting the inoculated plant tissue does not identify any moisture or damp spots on the paper). The *Agrobacterium*-inoculated plant tissue or cell thereof then can be co-cultivated on a surface in a desiccating environment.

In additional embodiments, the term "extreme desiccating environment" means co-cultivating the *Agrobacterium*-inoculated plant tissue or cell thereof a surface comprising at least one dry, absorbent paper (e.g., filter paper), wherein the dry paper is changed periodically throughout the co-cultivation. "Periodically," as used herein, means, for example, hourly, daily (i.e., each day), every two days, every three days, and the like. Thus, in some embodiments, the co-cultivating comprises culturing said *Agrobacterium*-inoculated sugar cane tissue or cell thereof on at least one layer of dry paper. In other embodiments, the co-cultivating comprises culturing the *Agrobacterium*-inoculated sugar cane tissue or cell thereof on two or more layers of dry paper. In further embodiments, the co-cultivating comprises culturing the *Agrobacterium*-inoculated sugar cane tissue or cell thereof on at least one layer of dry paper wherein the dry paper is changed periodically during co-cultivation. In still further embodiments, the co-cultivating comprises culturing the *Agrobacterium*-inoculated sugar cane tissue or cell thereof on two or more layers of dry paper, wherein the dry paper is changed periodically during co-cultivation. In other embodiments, the co-cultivating comprises culturing the *Agrobacterium*-inoculated sugar cane tissue or cell thereof on at least one layer of dry paper wherein the dry paper is changed each day during co-cultivation. In still other embodiments, the co-cultivating comprises culturing the *Agrobacterium*-inoculated sugar cane tissue or cell thereof on two or more layers of dry paper, wherein the dry paper is changed each day during co-cultivation. In yet other embodiments, the co-cultivating comprises culturing said *Agrobacterium*-inoculated sugar cane tissue or cell thereof on said surface in the absence of dry paper.

Accordingly, in some embodiments of the present invention, the inoculated tissue or cell thereof is co-cultivated on a surface in a desiccating environment and/or an extreme desiccating environment for a time period sufficient to reduce the original weight of the inoculated plant tissue by less than 1%, by about 1%, about 5%, about 10%, about 15%, about 20%, about 25% about 30%, about 35%, about 40%, about 45%, about 50%, about 55%, about 60%, about 65%, about 70%, about 75%, about 80%, and the like. In other embodiments, the original weight is reduced by more than about 35% up to about 60%, for example, about 36%, 37%, 38%, 39%, 40%, 41%, 42%, 43%, 44%, 45%, 46%, 47%, 48% 49%, 50%, 51%, 52%, 53%, 54%, 55%, 56%, 57%, 58%, 59%, 60%, and other such values between about 35% and about 60%. In some embodiments, the original weight is reduced by less than 1% to about 10%, by more than about 1% to about 10%, about 1% to about 15%, about 1% to about 19%, about 1% to about 20%, about 1% to about 25%, about 1% to about 30%, about 1% to about 40%, about 1% to about 50%, about 1% to about 55%, about 1% to about 60%, about 1% to about 70%, about 1% to about 80%, about 10% to about 20%, about 10% to about 25%, about 10% to about 30%, about 10% to about 40%, about 10% to about 50%, about 10% to about 60%, about 10% to about 70%, about 10% to about 80%, about 15% to about 25%, about 15% to about 30%, about 15% to about 40%, about 15% to about 50%, about 15% to about 60%, about 15% to about 70%, about 15% to about 80%, about 20% to about 30%, about 20% to about 40%, about 20% to about 50%, about 20% to about 60%, about 20% to about 70%, about 20% to about 75%, about 20% to about 80%, about 30% to about 40%, about 30% to about 50%, about 30% to about 60%, about 30% to about 65%, about 30% to about 70%, about 30% to about 80%, about 40% to about 50%, about 40% to about 60%, about 40% to about 70%, about 40% to about 80%, about 50% to about 60%, about 50% to about 65%, about 50% to about 70%, about 50% to about 75%, about 50% to about 80%, about 60% to about 65%, about 60% to about 70%, about 60% to about 75%, about 60% to about 80%, about 65% to about 70%, about 65% to about 80%, about 75% to about 80%, and the like and other such values between about 1% and about 80%. In some embodiments, the original weight is reduced by more than about 1% to about 13%, by more than about 1% to about 19%, by more than about 36% to about 50%.

In further embodiments, the inoculated tissue or cell thereof is co-cultivated on a surface in a desiccating and/or extreme desiccating environment for a time period sufficient to reduce the original weight of the inoculated plant tissue by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, and the like. Thus, in some embodiments, the original weight is reduced by at least about 35%. In additional embodiments, the original weight is reduced by at least about 55%.

Accordingly, in some embodiments, the original weight of said *Agrobacterium*-inoculated sugar cane tissue or cell thereof is reduced by more than about 1% to about 55%. In still further embodiments, the original weight of said *Agrobacterium*-inoculated sugar cane tissue or cell thereof is reduced by more than about 1% to about 10%. In additional embodiments, the original weight of said *Agrobacterium*-inoculated sugar cane tissue or cell thereof is reduced by at least 35%. In other embodiments, the original weight of said *Agrobacterium*-inoculated sugar cane tissue or cell thereof is reduced by at least 55%. Thus, for example, where the original weight of the inoculated plant tissue is 20 grams, the time period of the co-cultivation step in the desiccating environment is sufficient to reduce the weight of the inoculated tissue by more than about 35% (i.e, to a weight of less than about 13 grams). Desiccation of the plant tissue or cell thereof during co-cultivation to reduce the original weight of the plant tissue or cell thereof as described herein significantly improves transformation efficiency of sugar cane.

By "original weight" is intended the weight of the *Agrobacterium*-inoculated sugar cane tissue or cell thereof prior to the start of the transformation process. In some embodiments, the transformation process begins with exposing the sugar cane tissue or cell thereof to a temperature shock, as described below. In other embodiments of the invention, the tissue is not exposed to temperature shock and the transformation process begins with the addition of *Agrobacterium* or other appropriate bacterium to the sugar cane tissue or cell thereof. Thus, the "original weight" refers to the weight of the tissue that is determined prior to inoculation. Accordingly, a reduction in original weight as used herein refers to the weight of the plant tissue taken prior to inoculation with an inoculation suspension comprising *Agrobacteria* as compared to the weight of the tissue determined after co-cultivation with the bacteria. Based on the weight that is determined at these two time points (i.e., prior to inoculation and after co-cultivation), a percentage in reduction of original weight can be determined.

The time period sufficient to reduce the original weight of the *Agrobacterium*-inoculated plant tissue will depend upon the size of the inoculated plant tissue, the type of tissue (for example, callus tissue versus meristematic tissue), and physical parameters associated with the desiccating or extreme desiccating environment. Thus, for example, the environment may be manipulated to accelerate the desiccation of inoculated plant tissue. In some embodiments, the co-cultivation step may be performed in the presence of air flow (e.g., in a laminar hood or near a fan) to accelerate evaporation, in the presence of a vacuum, or in the presence of a suitable desiccant (e.g., calcium oxide, sulfuric acid, silica gel, etc.).

In some embodiments, the co-cultivation time period can be about 1 day to about 14 days, about 2 days to about 14 days, about 2 days to about 12 days, about 2 days to about 10 days, about 2 days to about 8 days, about 2 days to about 6 days, about 2 days to about 4 days, about 3 days to about 14 days, about 3 days to about 12 days, about 3 days to about 10 days, about 3 days to about 8 days about 3 days to about 6 days, about 3 days to about 4 days, about 4 days to about 14 days, about 4 days to about 12 days, about 4 days to about 10 days, about 4 days to about 8 days, about 4 days to about 6 days, about 5 days to about 14 days, about 5 days to about 12 days, about 5 days to about 10 days, about 5 days to about 8 days about 5 days to about 6 days, about 6 days to about 14 days, about 6 days to about 12 days, about 6 days to about 10 days, about 6 days to about 8 days, about 7 days to about 14 days, about 7 days to about 12 days, about 7 days to about 10 days, about 7 days to about 8 days, about 8 days to about 14 days, about 8 days to about 12 days, about 8 days to about 10 days, about 9 days to about 14 days, about 9 days to about 12 days, about 9 days to about 10 days, about 10 days to about 14 days, about 10 days to about 12 days, and the like. In other embodiments, the co-culture period can be for 1 day, 2 days, 3 days, 4 days, 5 days, 6 days, 7 days, 8 days, 9 days, 10 days, 11 days, 12 days, 13 days, or 14 days. In some embodiments, the co-cultivation time period described above can be combined in various embodiments with the changes in original weight of the plant tissue or cell thereof as described above. Thus, any of the co-cultivation time periods can be combined with any of the changes in original weight of the plant tissue or cell thereof as described above and/or with the addition of liquid to the co-cultivation as described above.

During the co-cultivation step, the temperature can be any suitable temperature for co-cultivation as known in the art. Thus, in representative embodiments, the temperature can be in a range from about 15° C. to about 30° C., from about 16° C. to about 29° C., from about 17° C. to about 28° C., from about 18° C. to about 27° C., from about 19° C. to about 26° C., from about 20° C. to about 28° C., from about 20° C. to about 25° C., from about 21° C. to about 24° C., or from about 22° C. to about 23° C. Thus, in some embodiments, the temperature during co-cultivation can be about 15° C., 16° C., 17° C., 18° C., 19° C., 20° C., 21° C., 22° C., 23° C., 24° C., 25° C., 26° C., 27° C., 28° C., 29° C., 30° C., and the like, and any combination thereof. In some embodiments, the temperature during the co-cultivation step is about 20° C. to about 28° C., and the time period of co-cultivation is about 3 days to about 5 days; in other embodiments, the temperature during the co-cultivation step is about 23° C., about 24° C., or about 25° C. and the time period of co-cultivation is from about 3 days to about 5 days. In other embodiments, the co-cultivation step is about 23° C., about 24° C., or about 25° C. and the time period of co-cultivation is about 3 days. In yet other embodiments, the co-cultivation step is about 23° C., about 24° C., or about 25° C. and the time period of co-cultivation is about 4 days. In still other embodiments, the co-cultivation step is about 23° C., about 24° C., or about 25° C. and the time period of co-cultivation is about 5 days. In some embodiments, the co-cultivation step occurs in the dark (i.e., in the absence of an external light source).

As used herein, "about" means within a statistically meaningful range of a value such as a stated concentration range, time frame, weight (e.g., a percentage change (reduction or increase in weight), volume, temperature or pH. Such a range can be within an order of magnitude, typically with 20%, more typically still within 10%, and even more typically within 5% of a given value or range. The allowable variation encompassed by "about" will depend upon the particular system under study, and can be readily appreciated by one of skill in the art.

As used herein, "a," "an" or "the" can mean one or more than one. For example, "a" cell can mean a single cell or a multiplicity of cells.

As used herein, "and/or" refers to and encompasses any and all possible combinations of one or more of the associated listed items, as well as the lack of combinations when interpreted in the alternative ("or").

As used herein, the term "polypeptide" encompasses both peptides and proteins, unless indicated otherwise.

As used herein, an "isolated" polypeptide or polypeptide fragment means a as polypeptide or polypeptide fragment separated or substantially free from at least some of the other components of the naturally occurring organism, for example, the cellular components or other polypeptides or nucleic acids commonly found associated with the polypeptide. In representative embodiments of the invention an "isolated" polypeptide, polypeptide fragment and/or protein is at least about 5%, 10%, 15%, 20%, 25%, 30%, 40%, 50%, 60%, 70%, 75%, 80%, 85%, 90%, 95%, 97%, 98%, 99% pure (w/w) or more.

As used herein "nucleic acid" is a macromolecule composed of chains of monomeric nucleotides including, but not limited to deoxyribonucleic acid (DNA) and ribonucleic acid (RNA). A nucleic acid can include a gene. In particular embodiments, the nucleic acids used in the present invention are "isolated" nucleic acids. As used herein, an "isolated" nucleic acid means a nucleic acid separated or substantially free from at least some of the other components of the naturally occurring organism, such as for example, the cell structural components or other polypeptides or nucleic acids commonly found associated with the nucleic acid. In particular embodiments, the "isolated" nucleic acid is at least about 1%, 5%, 10%, 25%, 50%, 60%, 70%, 75%, 80%, 85%, 90%, 95%, 97%, 98%, 99% or more pure (w/w). In other embodiments, an "isolated" nucleic acid indicates that at least about a 5-fold, 10-fold, 25-fold, 100-fold, 1000-fold, 10,000-fold, 100,000-fold or more enrichment of the nucleic acid (w/w) is achieved as compared with the starting plant material/tissue or cell thereof.

As used herein, the term "expression" (and grammatical equivalents) with reference to a nucleic acid refers to transcription of the nucleic acid and, optionally translation.

As used herein, the transitional phrase "consisting essentially of" means that the scope of a claim is to be interpreted to encompass the specified materials or steps recited in the claim" and those that do not materially affect the basic and novel characteristic(s)" of the claimed invention. Thus, the term "consisting essentially of" when used in a claim of this invention is not intended to be interpreted to be equivalent to "comprising."

Various embodiments of the invention are described herein. Any of the features of the various embodiments of the invention described herein can be combined, creating additional embodiments which are intended to be within the scope of the invention.

Co-cultivation occurs on a suitable surface in a desiccating or extreme desiccating environment. Exemplary surfaces include, but are not limited to, the surface of a vessel, flask, dish, e.g., a petri or culture dish, a container, and the like. Such vessels can be comprised of any suitable material including, but not limited to, glass, porcelain, plastics (e.g., polystyrene), and the like. Other suitable surfaces include dry absorbent paper (e.g., filter paper (i.e., a porous paper suitable for use as a filter paper (e.g., Whatman® brand filter paper)), seed germination paper, paper towel, blot paper, coffee filter, napkin and the like).

Where paper is the surface, it is recognized that one or more layers of the paper may be utilized to facilitate the desiccation of the inoculated plant tissue or cell thereof, for example, by acting as an absorption wick. Thus, for example, in some embodiments, the surface used during the co-cultivation step comprises, consists essentially of and/or consists of at least one layer of a dry paper (e.g., dry filter paper). In other embodiments, the surface used during the co-cultivation step comprises, consists essentially of and/or consists of two layers of a dry paper or three layers of a dry paper. In other embodiments, the surface used during the co-cultivation step comprises, consists essentially of and/or consists of four, five, six, seven, eight, nine, ten or more layers of dry paper. Where paper serves as the surface, it may be contained within any suitable vessel, flask, dish (e.g., petri, tissue culture), container, and the like. It is also recognized that the surface to be used in the co-cultivation step may be sterilized before use, using any suitable sterilization method known to those of skill in the art.

Thus, in some embodiments of the present invention, the co-cultivating comprises culturing said *Agrobacterium*-inoculated sugar cane tissue or cell thereof on at least one layer of dry filter paper. In other embodiments, the co-cultivating comprises culturing said *Agrobacterium*-inoculated sugar cane tissue or cell thereof on two or more layers of dry filter paper. In still other embodiments of the present invention, co-cultivating comprises culturing said *Agrobacterium*-inoculated sugar cane tissue or cell thereof on a surface in the absence of paper (e.g., in the absence of filter paper).

In addition, as described above, the co-cultivating can comprise culturing said *Agrobacterium*-inoculated sugar cane tissue or cell thereof on at least one layer of dry paper, wherein the dry paper is changed periodically throughout the co-cultivation. "Periodically," as used herein, means, for example, hourly, daily, every two days, every three days, and the like. Thus, in some embodiments, the co-cultivating comprises culturing said *Agrobacterium*-inoculated sugar cane tissue or cell thereof on at least one layer of dry paper, wherein the dry paper is changed daily during co-cultivation.

In some embodiments, wherein the environment is a desiccating environment, small amounts of sterile water or liquid medium, generally not more than about 20 ul, about 50 ul, about 75 ul, about 100 ul, about 200 ul, about 300 ul, about 400 ul, about 500 ul, about 600 ul, about 700 ul, about 800 ul, about 900 ul or about 1000 ul can be added at the co-cultivation step. Any of the liquid amounts described herein can be used in combination with any change in percent weight of the inoculated plant tissue or cell thereof as described above.

The addition of small amounts of sterile water or liquid medium as described herein can be added to slow, reduce or attenuate the rate of desiccation. In some embodiments, the co-cultivating in a desiccating environment comprises culturing said *Agrobacterium*-inoculated sugar cane tissue or cell thereof on at least one layer of dry paper comprising up to 1000 µl of liquid. In other embodiments, the co-cultivating in a desiccating environment comprises culturing said *Agrobacterium*-inoculated sugar cane tissue or cell thereof on at least one layer of filter paper comprising less than 50 µl of liquid.

The *Agrobacterium*-mediated transformation methods of the present invention are applicable to plants of the genus *Saccharum* (i.e., sugar cane, energy cane) and hybrids thereof, including hybrids between plants of genus *Saccharum* and those of related genera, such as *Miscanthus, Erianthus, Sorghum* and others. As used herein, "sugar cane" and "*Saccharum* spp." mean any of six to thirty-seven species (depending on taxonomic interpretation) of tall perennial grasses of the genus *Saccharum*. In particular, the plant can be *Saccharum aegyptiacum, Saccharum esculentum, Saccharum arenicol, Saccharum arundinaceum, Saccharum barberi, Saccharum bengalense, Saccharum biflorum, Saccharum chinense, Saccharum ciliate, Saccharum cylindricum, Saccharum edule, Saccharum elephantinum, Saccharum exaltatum, Saccharum fallax, Saccharum fallax, Saccharum floridulum, Saccharum giganteum, Saccharum hybridum, Saccharum japonicum, Saccharum koenigii, Saccharum laguroides, Saccharum munja, Saccharum narenga, Saccharum officinale, Saccharum officinarum, Saccharum paniceum, Saccharum pophyrocoma, Saccharum purpuratum, Saccharum ravennae, Saccharum robustum, Saccharum roseum, Saccharum sanguineum, Saccharum sara, Saccharum sinense, Saccharum spontaneum, Saccharum tinctorium, Saccharum versicolor, Saccharum violaceum, Saccharum violaceum*, and any of the interspecific hybrids and commercial varieties thereof.

In addition, the present invention provides methods for *Agrobacterium*-mediated transformation of any plant and, in particular, may be used to increase the efficiency of *Agrobacterium*-mediated transformation or may be used to make a particular plant less recalcitrant to *Agrobacterium*-mediated transformation. Examples of such plants include, but are not limited to, barley, beans in general, *Brassica* spp., clover, cocoa, coffee, cotton, flax, maize, millet, peanut, rape/canola, rice, rye, safflower, sorghum, soybean, sugar beet, sunflower, sweet potato, tea and wheat; vegetables including, but not limited to, cucurbits, broccoli, brussel sprouts, cabbage, carrot, cassava, cauliflower, lentils, lettuce, pea, peppers, pineapple, potato, radish and tomato; grasses including, but not limited to, alfalfa, bermudagrass, elephantgrass, rhodesgrass, tall fescue grass, tall wheat grass, *Miscanthus* spp. and switchgrass; tree fruits including, but not limited to, apples, apricots, avocado, banana, citrus, coconuts, pears, peaches and walnuts; and flowers including, but not limited to, carnations, orchids and roses.

In some embodiments, a plant, plant part, plant tissue for use in the *Agrobacterium*-mediated transformation methods of the invention means plant organs (e.g., leaves, stems, roots, etc.), seeds, plant cells, and progeny of the same. Thus, plant, plant part, plant tissue also includes, without limitation, protoplasts, nodules, callus (e.g., embryogenic callus tissue), suspension culture, embryos, as well as flowers, ovules, stems, fruits, leaves, side shoots (also referred to as tillers), roots, root tips and the like originating in plants or their progeny. Plant cell includes, without limitation, a cell obtained from a seed, embryo, meristematic region, callus tissue, suspension culture, leaf, primary stalk, root, shoot, gametophyte, sporophyte, pollen and/or microspore. The plant, plant part, plant tissue of the present invention can be derived from greenhouse grown plants or from field grown plants.

In some embodiments, suitable plant tissue for use in the *Agrobacterium*-mediated transformation methods of the invention may be any plant-derived tissue or cell thereof that is amenable to regeneration of a whole plant following introduction of the nucleic acid of interest. In other embodiments, the plant tissue or cell thereof for use in the *Agrobacterium*-mediated transformation methods of the invention may be any plant-derived callus tissue or a cell thereof. Thus, in some embodiments, the plant tissue includes, but is not limited to, cell culture (e.g., cell suspension or suspension culture, callus tissue).

Exemplary sugar cane tissues include, but are not limited to, those derived from young leaf bases, immature flowers or inflorescences, axillary buds, isolated shoot or root meristems, immature leaf rolls/whorls, immature side shoots (also referred to as immature tillers or suckers), seeds, isolated embryos and the like. In some embodiments, the sugar cane tissue or cell thereof is obtained from a sugar cane stalk or tiller. In other embodiments, the sugar cane tissue can be immature leaf whorls excised from either a primary stalk or from a tiller of a sugar cane plant. In some embodiments, the sugar cane tissue is embryogenic callus tissue derived from the foregoing tissues. In other embodiments, the sugar cane tissue is embryogenic callus derived from young sugar cane tiller tissue (e.g., immature side shoots). In still other embodiments, the sugar cane tissue is obtained from a leaf roll segment or a leaf sheath segment excised from a stalk or tiller. In additional embodiments, the sugar cane tissue is embryogenic callus tissue or cell thereof derived from a leaf roll segment or a leaf sheath segment excised from a stalk or tiller. In further embodiments, the sugar cane as tissue is embryogenic callus tissue or cell thereof. In still further embodiments, the sugar cane tissue is embryogenic callus or cell thereof derived from immature leaf whorl tissue. Embryogenic callus is derived from the aforementioned plant tissues via methods of pre-culturing as known in the art and described below.

As used herein, "side shoot" means a shoot other than the primary shoot (i.e., stalk) originating from the crown of the sugar cane plant close to the soil surface. A side shoot may also be referred to as a "secondary shoot".

As described above, in some embodiments, the plant tissue or cell thereof can be derived from immature side shoots at the development stage where the lower internode is beginning to elongate. The age of the side shoot at this stage is typically between about one and six months old, including about one to about three months, about one to about four months, about one to about five months, about two to about three months, or about two to about four months old. In other embodiments, the age of the side shoot at this stage is between six months and 12 months old. Young or immature side shoots grow up from the base of maturing sugar cane plants, and the production of such side shoots can be induced by cutting back the maturing canes to the ground, as well as removing larger side shoots to promote growth of more side shoots. Accordingly, in some embodiments, young side shoots can be produced in large numbers in the greenhouse, making for a very consistent source of plant material for a transformation process. Use of side shoots for transformation and regeneration of transgenic plants significantly reduces the impact on the sugar cane growth and development since the entire primary stalk or portion thereof does not have to be removed for transformation purposes, and the sugar cane plant can continue to produce side shoots for a substantial length of time. This plant material can be processed and pretreated in many different ways to maximize its potential as a target for *Agrobacterium*-mediated transformation. Further, side shoots can be obtained from greenhouse-grown plants. In other embodiments, the plant tissues used with the present invention are derived from field grown plants.

Primary and side shoots can be excised from the plant and sterilized by standard methods as described herein and well known to one of skill in the art to establish sterile cultures in an artificial medium. For example, the side shoots can be contacted with a 70% ethanol solution, or a 20% bleach solution. Following sterilization of the excised side shoot, a segment, slice, or section of plant tissue is obtained. In some embodiments, the section may be about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 3 mm, about 4 mm, about 5 mm, about 6 mm, 7 mm, about 8 mm, about 9 mm, about 10 mm or greater in thickness. The plant tissue obtained in this way is often referred to as an "explant." The term "explant" refers to living tissue removed from an organism and placed in a medium for tissue culture.

In some embodiments, the explant may be obtained from primary stalk or side shoot tissues including leaf spindle or whorl, stems, leaf sheath, leaf roll (meristematic region), node, or internode segments. In some embodiments, the explant can be leaf sheath or leaf roll sections. The segment may be cut from just above the apical meristem up to about 10 mm to about 50 mm above the apical meristem. Thus, the segment may be cut from just above the apical meristem up to about 10 mm, up to about 20 mm, up to about 30 mm, up to about 40 mm, or up to about 50 mm above the apical meristem. In various embodiments, the explant is not a node segment or is not an internode segment. As used herein, "node segment" means any joint in a stem from which one or more leaves may grow and also includes any lateral (axillary) buds on the side of the stem, as in a leaf axil. The part of the stem between two nodes is termed the "internode." The outer one or two leaves may be removed from the side shoot prior to segmenting.

As mentioned above, in some embodiments, the present invention provides methods wherein the plant tissue can be subjected to a pre-culturing step in which the plant tissue is cultured in an appropriate pre-culture medium under conditions sufficient to produce embryogenic callus. Thus, in some embodiments of the invention the sugar cane tissue or cell thereof is obtained by pre-culturing a segment of said tiller for a period of time to produce embryogenic callus tissue prior to contacting said sugar cane tissue or cell thereof with said inoculation culture comprising *Agrobacterium*.

The term "callus" refers to an undifferentiated proliferating mass of cells or tissue. In various embodiments, the media is suitable for embryogenic callus induction. As used herein, "embryogenic callus" means tissues or cells that are undifferentiated and without significant structure but with the potential to form a more differentiated tissue (e.g., embryogenic tissue) that can produce embryos and germinate into plants.

Culture conditions sufficient for embryogenic callus formation are known to those skilled in the art, and may vary according to sugar cane cultivar. Suitable culture media for establishment and maintenance of embryogenic callus cultures are described in, for example, *Methods in Molecular Biology*, Vol. 344 (Wang, ed. Springer (2006)), pages 227-235; Published International Application No. WO 01/33943; U.S. Pat. Nos. 5,908,771; 6,242,257; Croy, ed. (1993) *Plant Molecular Biology Labfax* (Bios Scientific) Publishers, Ltd.); Jones, ed. (1995) *Plant Transfer and Expression Protocols* (Humana Press); and in the references cited therein. Each of these references is incorporated herein by reference in their entirety. Additional details relating to culturing plant cells, including pretreatment processes, are provided in the Experimental section below.

The plant tissue for transformation may be cultured from about 1 to about 100 days, inclusive, prior to inoculation with *Agrobacterium* or other suitable bacteria (i.e., pre-cultured). In various embodiments, the plant tissue can be cultured for about 5 days, about 6 days, about 7 days, about 8 days, about 9 days, about 10 days, about 12 days, about 14 days, about 16 days, about 18 days, about 20 days, about 25 days, about 30 days, about 35 days, about 40 days, about 45 days, about 50 days, about 55 days, about 60 days, about 65 days, about 70 days, about 75 days, about 80 days, about 85, days, about 90 days, about 95 days or about 100 days, and the like, prior to transformation. The culture medium may include Murashige and Skoog (MS) nutrient formulation (Murashige & Skoog (1962) *Physiologia Plantarum* 15:473-497) or Gamborg's medium (Gamborg et al. (1968) *Exp. Cell Res* 50:151-158). Preferably, the medium comprises MS nutrient formulation. It will be appreciated that the above-mentioned media are commercially available, as are other potentially useful media.

The medium may further comprise sucrose, and may additionally include agar. Thus, it will be appreciated that the plant tissue may be pre-cultured in solid or liquid medium.

Additional components of the pre-culture medium may include phytohormones such as cytokinin and/or auxin. In various embodiments, the cytokinin can be selected from the group consisting of kinetin and $N_6$-benzyladenine (BA), and combinations thereof. There are a variety of other cytokinin and/or cytokinin-like compounds that may be useful according to the present invention, e.g., zeatin, α-isopentyladenosine, and/or diphenylurea.

In various embodiments, the auxin is 1-napthaleneacetic acid (NAA) and/or 2,4 dichlorophenoxyacetic acid (2,4D). There are a variety of other auxins or auxin-like compounds that may be useful according to the present invention, for example indole-3-butyric acid (IBA), p-chlorophenoxyacetic acid (CPA), indole-3-acetic acid (IAA), 2,4,5-trichlorophenoxyacetic acid, phenylacetic acid, picloram, β-napthoxyacetic acid, dicamba and/or trans-cinnamic acid.

It will be readily apparent to the skilled artisan that the most efficacious concentrations of auxin and/or cytokinin can be determined empirically by cross-testing various concentrations of auxin and/or cytokinin. The optimal concentration of either or both can be tailored according to the particular plant cultivar from which the cultured plant tissue was taken.

Following initial embryogenic callus formation, high quality responses are optionally sub-cultured for about 1 to about 10 days, inclusive, to produce callus for transformation via *Agrobacterium* inoculation.

The plant tissue, e.g., embryogenic callus, then can be subjected to an inoculation step, as described herein, wherein the callus culture cells are contacted with an inoculation culture comprising a bacterium, for example, *Agrobacterium*, that comprise a nucleic acid of interest that is to be introduced into the sugar cane plant tissue.

Any suitable method for inoculating the sugar cane tissue or cell thereof to obtain an *Agrobacterium*-inoculated plant tissue or cell thereof and for selecting a transformed sugar cane tissue or cell thereof can be used in the methods of the present invention, including procedures known to one of skill in the art and those described below. The distinguishing feature of the transformation methods of the present invention is the subjection of the *Agrobacterium*-inoculated plant tissue or cell thereof to a co-cultivation step that includes culturing the inoculated plant tissue or cell thereof on a surface in a desiccating or extreme desiccating environment for a time period sufficient to reduce the original weight of the inoculated plant tissue or cell thereof as described above. Thus, any transformation protocol for sugar cane that comprises an inoculation step with an *Agrobacterium* comprising a nucleic acid of interest, a co-cultivation step, and a selection step, can be improved by modifying that method to include the co-cultivation protocol disclosed herein.

Many methods of *Agrobacterium*-mediated transformation of plants are known in the art. See, for example, U.S. Pat. Nos. 5,563,055 and 5,981,840; see also, Arencibia et al. (1998) *Transgenic Res.* 7:123-222; Arencibia & Carmona "Sugar cane (*Saccharum* spp.)," in *Methods in Molecular Biology, Agrobacterium Protocols*, Vol. 2, ed. Wang ($2^{nd}$ ed., Humana Press, Inc.), pages 227-235 (2007); de la Riva et al. (1998) *Electron. J. Biotechnol.* 1:118-133; Manickavasagam et al. (2004) *Plant Cell Rep.* 23:134-143; Opabode (2006) *Biotechnol. Mol. Biol. Rev.* 1:12-20; and Zhang et al. (2006) *J. Integr. Plant Biol.* 48:453-459).

As used herein, "Agrobacterium" means a species, subspecies, or strain of *Agrobacterium* that is able to mobilize and selectively transfer T-DNA into a plant or plant cell thereof. In particular embodiments, the *Agrobacterium* can be *Agrobacterium rhizogenes* (i.e., *Rhizobium rhizogenes*) or *A. tumefaciens*. Any strain of *Agrobacterium* capable of mobilizing and selectively transferring T-DNA into a plant or plant cell can be used in the present invention. In some embodiments, wild-type strains are used. In other embodiments, "disarmed" derivatives of *Agrobacterium* species, in which the tumor-inducing sequences of the Ti plasmid have been removed, are used. Examples of suitable *A. tumefaciens* strains include, but are not limited to, e.g., EHA101, as described by Hood et al. (1986) *J. Bacteriol.* 168:1291-1301); LBA4404, as described by Hoekema et al. (1983) *Nature* 303:179-180; and C58 (pMP90), as described by Koncz and Schell (1986) *Mol. Gen. Genet.* 204:383-396, EHA 105, AGLI and AGL0, SBI, and the like, and any combination thereof. Examples of suitable *Agrobacterium rhizogenes* strains include, but are not limited to, 15834, as described by Birot et al. (Biochem, 25: 323-35) and R1000. In further embodiments, in addition to *Agrobacterium* species and strains, other bacterial species and strains thereof, which are competent for nucleic acid transfer can be used in the methods of transformation of the present invention (see for example those described by CAMBIA (www.cambia.org); see also Broothaerts et al. *Nature* 433:629-633 (2005)). Non-limiting examples of non-*Agrobacterium* bacteria competent for nucleic acid transfer include *Sinorhizobium, Mesorhizobium* and *Rhizobium* (Id.).

Inoculation can be carried out according to any method known in the art, and typically involves mixing the sugar cane tissue or cell thereof with an inoculation culture that comprises a bacterium strain (e.g., *Agrobacterium*) that harbors a plasmid or vector comprising a nucleic acid of interest. A typical inoculation culture is an inoculation suspension that has been prepared from cultured *Agrobacterium*. In this manner, the *Agrobacterium* strain harboring the nucleic acid of interest to be transformed into the sugar cane plant tissue or cell thereof is cultured on an appropriate culture medium supplemented with antibiotics selective for the strain and vector (see, for example, the protocol described in the Experimental section herein below). Those of skill in the art are familiar with procedures for growth of *Agrobacterium* and suitable culture conditions. Typically an *Agrobacterium* culture is inoculated from a glycerol stock or streaked plate and is grown overnight. The bacterial cells are then washed and resuspended in a culture medium suitable for inoculation of the sugar cane tissue or cell thereof. As used herein "inoculation suspension" means a suspension of bacterial cells (e.g., *Agrobacterium* spp.) to be used for inoculating plant tissue or cell thereof. "Inoculation culture" refers to the combination of the bacterial cells and plant tissue or cells thereof.

Inoculation (i.e., infection) itself can be for at least about one minute to about twelve hours (i.e., overnight) at about room temperature (i.e., at about 20° C. to about 25° C.). During inoculation, it is contemplated that various additional treatments can be applied to aid with *Agrobacterium* infection such as sonication or vacuum infiltration of the inoculation culture. For example, the inoculation culture can be sonicated as described in Trick and Finer (1998) *Plant Cell Rep.* 17:482-488, and U.S. Pat. No. 5,693,512. Alternatively, or in addition, the inoculation culture can be vacuum infiltrated as described in Amoah et al. (2001) *J. Exp. Bot.* 52:1135-1142 and Park et al. (2005) *Plant Cell Rep.* 24:494-500).

In some embodiments, it is contemplated that the sugar cane tissue is subjected to a temperature differential pretreatment prior to inoculation. By "temperature differential pretreatment" is intended the sugar cane tissue or cell thereof is exposed to a temperature, higher than the temperature at which inoculation will be carried out. Thus, for example, where inoculation is to be carried out at about room temperature (e.g., about 20° C. to about 25° C.), the temperature differential pretreatment can comprise exposure of the sugar cane tissue or cell thereof to a temperature that is about 5° C., about 10° C., about 15° C., about 20° C., about 25° C., or about 30° C. higher (in which case the sugar cane tissue or cell thereof is exposed to a heat pretreatment; ie., heat shock) than the temperature at which inoculation will be carried out (for example, room temperature). The length of the temperature differential pretreatment will vary depending upon the type and source of the sugar cane tissue. Thus, in some embodiments, the length of the temperature differential pretreatment is about 1 minute to about 60 minutes, 1 minute to about 50 minutes, 1 minute to about 40 minutes, 1 minute to about 30 minutes, about 1 minute to about 20 minutes, about 1 minute to about 15 minutes, about 1 minute to about 10 minutes, or about 1 minute to about 5 minutes. In other embodiments, the length of the temperature differential pretreatment is 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 60 min, and the like.

Thus, in some embodiments, it is contemplated that the sugar cane tissue or cell thereof is pretreated with a heat shock prior to inoculation using methods known to those of skill in the art. Thus, as a non-limiting example, heat shock comprises contacting the plant tissue or cell thereof with medium such as basic medium (e.g., Murashige and Skoog medium; Murashige and Skoog (1962) *Physiol. Plant* 15:473-497) pre-warmed to a temperature of about 35° C. to about 55° C., for about 1 minute to about 15 minutes. In another non-limiting example, heat shock comprises contacting the plant tissue or cell thereof with media pre-warmed to a temperature of about 45° C. for about 5 minutes.

Following the co-cultivation step, and prior to selecting and regenerating transgenic plant parts or plants, the *Agrobacterium*-inoculated plant tissue optionally can be allowed to "rest" by culturing the inoculated plant tissue in a resting medium. As used herein, "resting medium" means a medium for culturing inoculated plant tissue or cell thereof after co-cultivation typically comprises agents that can inhibit or suppress the growth and metabolic activity of the bacteria or kill the bacteria (e.g., bacteriostatic or bactericidal agents). As used herein, "bacteriostatic" means capable of inhibiting or suppressing the growth or reproduction of bacteria. In contrast, "bactericidal" means capable of killing bacteria outright. The constituents of such a medium are generally known in the art. For example, the resting medium can be a basal medium (e.g., Murashige and Skoog (MS) medium) supplemented with timentin and/or other antibiotic including, but not limited to, cefotaxime and/or carbenicillin. See also, Zhao et al. (2001) *Molecular Breeding* 8:323-333.

Accordingly, in the resting step, the *Agrobacterium*-inoculated plant tissue or cell thereof can be cultured in the resting medium for about 1 day to about 15 days, about 2 days to about 14 days, about 2 days to about 12 days, about 2 days to about 11 days, about 2 days to about 10 days, about 3 days to about 10 days, about 4 days to about 10 days, about 5 days to about 10 days, about 6 days to about 9 days, or about 6 days to about 8 days. Thus, following the co-cultivation step, the inoculated plant tissue or cell thereof can be cultured in the resting medium for about 1 day, 2 days, 3 days, 4 days, 5 days, 6 days, 7 days, 8 days, 9 days, 10 days, 11 days, 12 days, 13 days, about 14 days, or about 15 days. In some embodiments, no resting step is included, and instead, following co-cultivation, the plant tissue or cell thereof is subjected to selection as described below. In some embodiments, the selection medium can include at least one compound that suppress the growth of and/or kill the bacteria.

In representative embodiments, following inoculation and co-cultivation, and optionally culturing in a resting medium, subsequent selecting and regenerating steps can be by any methods known in the art. See, e.g., McCormick et al. (1986) *Plant Cell Rep.* 5:81-84. For example, the plant material can be transferred to a medium that includes a selective agent capable of preventing the growth of cells that have not received a target polynucleotide (for example, a polynucleotide encoding a polypeptide of interest and/or a nucleotide sequence conferring resistance to a selection agent) of which at least one expression product is capable of preventing the action of a selective agent to thereby select for transformed plant cells. As used herein, "selecting" means a process in which one or more plants, plant tissues, or plant cells are identified as having one or more properties of interest, for example, a selectable marker or a scorable marker, enhanced insect resistance, increased or decreased carotenoid levels, altered coloration, etc. For example, a selection process can include placing organisms under conditions where the growth of those with a particular genotype will be favored.

The selection step can comprise culturing under selective conditions the plant callus tissue and/or cell thereof that was exposed to the nucleotide sequence of interest, wherein the selective conditions include those that are sufficient for distinguishing a transformed cell from a non-transformed cell. Such conditions will vary with, for example, the type of selectable marker used, the cultivar, and the plant material targeted for transformation, but will generally comprise conditions that favor the growth of transformed cells but inhibit the growth of non-transformed cells.

For example, in representative embodiments, during the selection process, the *Agrobacterium*-inoculated plant material can be exposed to sub-lethal levels of a selective agent for about 2 weeks to about 12 weeks, and then to lethal levels of the selective agent for about 4 weeks to about 30 weeks in a step-wise selection process.

The nucleic acid encoding the selectable marker may be on the same expression cassette as the nucleotide sequence of interest, or may be co-transformed on a separate expression cassette. Selectable markers and selection agents are known in the art. Non-limiting examples of nucleic acids encoding selectable markers used routinely in transformation include the nucleic acid encoding nptII, which confers resistance to kanamycin and related antibiotics (Messing and Vierra (1982) *Gene* 19:259-268; Bevan et al. (1983) *Nature* 304: 184-187); the nucleic acid encoding bar, which confers resistance to the herbicide phosphinothricin (White et al. (1990)

*Nucleic Acids Res.* 18:1062; Spencer et al. (1990) *Theor. Appl. Genet.* 79:625-631); the nucleic acid encoding hph, which confers resistance to the antibiotic hygromycin (Blochinger and Diggelmann (1984) *Mol. Cell. Biol.* 4:2929-2931); the nucleic acid encoding dhfr, which confers resistance to methatrexate (Bourouis et al. (1983) *EMBO J.* 2(7): 1099-1104); the nucleic acid encoding EPSPS, which confers resistance to glyphosate (U.S. Pat. Nos. 4,940,935 and 5,188,642), and the nucleic acid encoding phosphomannose isomerase (PMI), which confers the ability to metabolize mannose (U.S. Pat. Nos. 5,767,378 and 5,994,629).

Thus, in some embodiments, the present invention provides methods of producing a transformed sugar cane tissue or cell thereof comprising: inoculating a sugar cane tissue or cell thereof with *Agrobacterium*, said *Agrobacterium* comprising a nucleic acid of interest, to obtain an *Agrobacterium*-inoculated sugar cane tissue or cell thereof, wherein the nucleic acid of interest comprises an expression cassette comprising a nucleic acid that confers resistance to a selection agent; co-cultivating said *Agrobacterium*-inoculated sugar cane tissue or cell thereof on a surface in the absence of co-culture media for a time period sufficient to reduce original weight of said *Agrobacterium*-inoculated sugar cane tissue or cell thereof; and selecting a transformed sugar cane tissue or cell thereof comprising said nucleic acid of interest, wherein the selecting comprises culturing said *Agrobacterium*-inoculated sugar cane tissue in a medium comprising said selection agent, and selecting a transformed sugar cane tissue or cell thereof comprising said nucleic acid of interest.

Plant tissue or a cell thereof growing in the presence of a selective agent can be further manipulated for plant regeneration. As used herein, "regenerate," "regeneration," and "regenerating" (and grammatical variations thereof) means formation of a plant from various plant parts (e.g., plant explants, callus tissue, plant cells) that includes a rooted shoot. The regeneration of plants from various plant parts is well known in the art. See, e.g., *Methods for Plant Molecular Biology* (Weissbach et al., eds. Academic Press, Inc. (1988); for regeneration of sugar cane plants, see, for example, Arencibia et al. (*Trans. Res.* 7:213-222 (1998)); Elliot et al. (*Plant Cell Rep.* 18:707-714 (1999)); and Enriquez-Obregon et al. (*Planta* 206:20-27 (1998)). For example, regenerating plants containing a nucleic acid of interest introduced by *Agrobacterium* from leaf explants can be achieved as described by Horsch et al. (1985) *Science* 227:1229-1231. Briefly, transformants are grown in the presence of a selection agent and in a medium that induces the regeneration of shoots (e.g., in sugar cane). See, for example, Fraley et al. (1983) *Proc. Natl. Acad. Sci. USA* 80:4803-4807. This method typically produces shoots within about two weeks to four weeks, and the transformed shoots are then transferred to an appropriate root-inducing medium containing the selective agent and an antibiotic to prevent further bacterial growth. Typically, transformed shoots that root in the presence of the selective agent to form plantlets are then transplanted to soil or other media to allow the production of additional roots. (For references to regeneration of sugar cane, see, Lakshmann et al. *In Vitro Cell Devel Biol* 41:345-363 (2005))

The transgenic plantlets are then propagated in soil or a soil substitute to promote growth into a mature transgenic plant. Propagation of transgenic plants from these plantlets is performed, e.g., in perlite, peatmoss and sand (1:1:1) or commercial plant potting mix under glasshouse conditions.

As described above, the transformation methods of the invention provide for the introduction of a nucleic acid of interest into a sugar cane plant, plant part and/or plant tissue.

"Introducing" in the context of a nucleotide sequence of interest means presenting the nucleotide sequence of interest to the plant, plant part, or plant tissue in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different transformation vectors. Accordingly, these polynucleotides can be introduced into sugar cane plant cells in a single transformation event, in separate transformation events, or, e.g., as part of a breeding protocol.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. The genome as used herein also includes the plastid genome, and therefore includes integration of the nucleic acid into, for example, the chloroplast genome. Stable transformation as used herein can also refer to a transgene that is maintained extrachromasomally, for example, as a minichromosome.

In accordance with the methods of the present invention, a nucleic acid of interest is introduced into a bacterial strain competent for nucleic acid transfer (e.g., an *Agrobacterium* strain) via conventional transformation methods, and the bacterial strain is then utilized in the transformation methods of the invention to introduce the nucleic acid of interest into a sugar cane plant, plant part, tissue, or cell. Many vectors are available for transformation of *Agrobacterium*. These typically carry at least one T-DNA border sequence and include vectors such as pBIN19 (Bevan, *Nucleic Acids Res.* 12:8711-8721 (1984)). For the construction of vectors useful in *Agrobacterium* transformation, see, for example, U.S. Patent Application Publication No. 2006/0260011, herein incorporated by reference in its entirety.

*Agrobacterium* transformation typically involves the transfer of a binary vector carrying the foreign nucleic acid of interest to an appropriate *Agrobacterium* strain which may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* is accomplished by a tri-parental mating procedure using *E. coli* carrying the recombinant binary vector, a helper *E. coli* strain that carries a plasmid and which is able to mobilize the recombinant binary vector to the target *Agrobacterium* strain. Alternatively, the recombinant binary vector can be transferred to *Agrobacterium* by DNA transformation (Hofgen and Willmitzer (1988) *Nucleic Acids Res.* 16:9877).

Any nucleic acid of interest can be transformed into the *Agrobacterium* strain or other bacterial strain competent for nucleic acid transfer for subsequent transformation of sugar cane using the methods of the present invention. In some embodiments, the nucleic acid will be a polynucleotide construct comprising an expression cassette that comprises functional elements that allow for expression of a polynucleotide of interest in sugar cane following its introduction via the *Agrobacterium*-mediated transformation methods of the present invention.

An expression cassette can comprise a nucleic acid encoding a polynucleotide that confers a property that can be used to detect, identify or select for transformed plant cells and tissues (e.g., a marker for the selection of transformed cells). The nucleic acid encoding the marker may be on the same expression cassette as the nucleotide sequence of interest, or may be co-transformed on a separate expression cassette. In some embodiments, the nucleic acid encoding the marker can be the nucleotide sequence of interest. Thus, in some embodiments of the present invention, the nucleic acid of interest comprises an expression cassette that further comprises a nucleotide sequence conferring resistance to a selection agent, and thus, selecting comprises culturing the *Agrobacterium*-inoculated sugar cane tissue or cell thereof in a medium comprising the selection agent, and selecting a transformed sugar cane tissue or cell thereof comprising the nucleic acid of interest.

In other embodiments, the nucleic acid can be a polynucleotide construct comprising an expression cassette that comprises a functional polynucleotide. As used herein, "functional polynucleotide" means a polynucleotide that can be transcribed, but not translated, such as an inhibitory nucleic acid.

Inhibitory nucleic acids can inhibit the expression of a polypeptide of interest such as those described below. The inhibitory nucleic acids may inhibit the expression of a polypeptide directly, by preventing translation of a messenger RNA encoding the polypeptide (for example, sense suppression/cosuppression; antisense suppression; double-stranded RNA (dsRNA) interference via small interfering RNA, micro RNA or short hairpin RNA; amplicon-mediated interference; and ribozymes). In other embodiments, the nucleic acids can encode a polypeptide that inhibits the transcription or translation of a nucleic acid sequence encoding the polypeptide of interest. Methods for inhibiting or eliminating the expression of a gene product in mammalian cells are well known in the art, and any such method may be used in the present invention to inhibit the expression of the polypeptide of interest.

For sense suppression/cosuppression, an expression cassette can be designed to express a cosuppressing nucleic acid corresponding to a native nucleic acid encoding an polypeptide of interest in the "sense" orientation. The cosuppressing nucleic acid can correspond to all or part of the nucleic acid encoding the polypeptide of interest, all or part of the 5' and/or 3' untranslated region of the nucleic acid encoding the polypeptide of interest, or all or part of the coding sequence and untranslated regions of the nucleic acid encoding the polypeptide of interest. In general, the cosuppressing nucleic acid can comprise at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950 or 1000 nucleotides, or can be of any size up to and including the full length nucleic acid sequence encoding the polypeptide of interest. Where the cosuppressing nucleic acid comprises all or part of the coding region for the polypeptide of interest, the expression cassette can be designed to eliminate the start codon so that no functional polypeptide of interest will be transcribed from the cosuppressing nucleic acid. Overexpression of the cosuppressing nucleic acid can result in reduced expression of the nucleic acid encoding the polypeptide of interest.

For antisense suppression, an expression cassette can be designed to express an antisense nucleic acid complementary to all or part of a native nucleic acid encoding the polypeptide of interest. The antisense nucleic acid can correspond to all or part of a complement of the nucleic acid encoding the polypeptide of interest, all or part of a complement of the 5' and/or 3' untranslated region of the nucleic acid encoding the polypeptide of interest, or all or part of a complement of both the coding sequence and the untranslated regions of the nucleic acid encoding the polypeptide of interest. The antisense nucleic acid also can be fully complementary (i.e., 100% identical to the complement of the target nucleic acid sequence) or partially complementary (i.e., less than 100% identical to the complement of the target nuclide acid sequence) to the nucleic acid encoding the polypeptide of interest. Expression of the antisense nucleic acid can result in reduced expression of the nucleic acid encoding the polypeptide of interest.

Regardless of the type of antisense nucleic acid used, sequences of at least 15 nucleotides, 20, 25, 30, 35, 40, 45, 50, 75, 100, 150, 200, 250, 300, 350, 400, 450, 500, 550 nucleotides or greater can be used.

Efficiency of antisense suppression can be increased by including a poly-dT region in the expression cassette at a position 3' to the antisense sequence and 5' of the polyadenylation signal. See, U.S. Patent Application Publication No. 2002/0048814.

For dsRNA interference, a sense nucleic acid like that described above for cosuppression and an antisense nucleic acid fully or partially complementary to the sense nucleic acid sequence are expressed in the same cell, resulting in inhibition of the expression of a native nucleic acid encoding the polypeptide of interest. Expression of the sense and antisense nucleic acids can be accomplished by designing an expression cassette to comprise both sense and antisense sequences for the nucleic acid encoding the polypeptide of interest. Alternatively, separate expression cassettes can be used for the sense and antisense nucleic acids.

Regardless of the type of nucleic acid used for dsRNA interference, sequences of at least 15 nucleotides, 20, 25, 30, 35, 40, 45, 50, 75, 100, 150, 200, 250, 300, 350, 400, 450, 500, 550 nucleotides or greater can be used.

For amplicon-mediated interference, an amplicon expression construct can be designed having a nucleic acid sequence comprising a virus-derived sequence that contains all or part of a native nucleic acid encoding the polypeptide of interest. The viral sequences present in the transcription product of the amplicon expression cassette allow the transcription product to direct its own replication. The transcripts produced by the amplicon may be either sense or antisense relative to the nucleic acid sequence encoding the polypeptide of interest.

Regardless of the type of nucleic acid used for amplicon-mediated interference, sequences of at least 15 nucleotides, 20, 25, 30, 35, 40, 45, 50, 75, 100, 150, 200, 250, 300, 350, 400, 450, 500, 550 nucleotides or greater can be used.

For ribozymes, an expression construct can be designed to express a nucleic acid having catalytic activity toward a mRNA expressed by a native nucleic acid sequence encoding the polypeptide of interest. The catalytic nucleic acid causes the degradation of the mRNA or nucleic acid encoding the polypeptide of interest resulting in reduced expression of the polypeptide of interest.

Regardless of the type of nucleic acid used for ribozymes, sequences of at least 15 nucleotides, 20, 25, 30, 35, 40, 45, 50, 75, 100, 150, 200, 250, 300, 350, 400, 450, 500, 550 nucleotides or greater can be used.

For micro RNA (miRNA) interference, an expression construct can be designed to express a nucleic acid complimentary to a native nucleic acid sequence encoding the polypeptide of interest, such that the miRNA is transcribed, but not translated into the poypeptide of interest (i.e., a non-coding RNA). Each primary transcript (a pri-miRNA) is processed into a short stem-loop structure called a pre-miRNA and finally into a functional miRNA. miRNAs consist of about twenty-two to about twenty-three ribonucleotides. Mature miRNA are highly efficient at inhibiting the expression of the nucleic acid encoding the polypeptide of interest. Because mature miRNAs are partially complementary to one or more nucleic acids encoding the polypeptide of interest, they down-regulate gene expression by inhibiting translation or sometimes facilitating cleavage of the nucleic acids encoding polypeptide of interest.

For short hairpin RNA (shRNA) interference, an expression cassette can be designed to express a nucleic acid complimentary to a native nucleic acid encoding the polypeptide of interest that makes a tight hairpin turn that can be used to silence gene expression via RNA interference. shRNA interference also can be intron-containing hairpin RNA (ihpRNA) interference in which the expression cassette can be designed to express a nucleic acid encoding intron-spliced RNA with a hairpin structure.

Regardless of the type of shRNA used, sequences of at least 15 nucleotides, 20, 25, 30, 35, 40, 45, 50, 75, 100, 150, 200, 250, 300, 350, 400, 450, 500, 550 nucleotides or greater can be used.

The expression cassette for shRNA interference also can be designed such that the sense sequence and antisense sequence do not correspond to a nucleic acid sequence encoding the polypeptide of interest. Instead, the sense and antisense sequences flank a loop sequence that comprises a nucleotide sequence corresponding to all or part of the nucleic acid sequence encoding the polypeptide of interest. Thus, the loop region determines the specificity of the RNA interference. See, e.g., Int'l Patent Application Publication No. WO 02/00904.

In addition, transcriptional gene silencing (TGS) can be accomplished through use of shRNA molecules where an inverted repeat of the hairpin shares sequence identity with the promoter region of a nucleic acid encoding the polypeptide of interest to be silenced. Processing of the shRNA into short RNAs that can interact with the homologous promoter region may trigger degradation or methylation to result in silencing (see, for example, Aufsatz et al Proc. Natl. Acad. Sci. 99: 16499-16506 (2002), and Mette et al Embo J. 19: 5194-5201 (2000)).

The methods of the invention therefore comprise transformation of plant tissue or a cell thereof with one or more nucleic acid molecules of interest. In one embodiment, the nucleic acid comprises an expression cassette that comprises a nucleotide sequence encoding a polypeptide of interest and/or a functional polynucleotide of interest. As used herein, "expression cassette" means a nucleic acid capable of directing expression of a particular nucleotide sequence in a sugar cane cell, comprising a promoter operably linked to the nucleotide sequence of interest, which is optionally operably linked to termination signals. It also typically comprises sequences required for proper translation of the nucleotide sequence of interest. The coding region usually codes for a polypeptide of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one that is naturally occurring (e.g., derived from sugar cane), which in some embodiments has been obtained in a recombinant form useful for heterologous expression. Typically, however, the expression cassette is heterologous with respect to the sugar cane plant, e.g., the particular DNA sequence of the expression cassette does not occur naturally in a sugar cane plant and must have been introduced into the sugar cane plant, or an ancestor of the sugar cane plant, by a transformation event. The expression of the nucleotide sequence of interest in the expression cassette may be under the control of a constitutive promoter or of an inducible promoter that initiates transcription only when the sugar cane plant, tissue or cell is exposed to some particular external stimulus. Additionally, the promoter can also be exclusively or preferentially expressed in specific cells, specific tissues, or specific organs or exclusively or preferentially expressed in a particular stage of development.

The expression cassette may include in the 5'-3' direction of transcription, a transcriptional and translational initiation region (i.e., a promoter) and a polynucleotide of interest. The expression cassette may optionally comprise a transcriptional and translational termination region (i.e., termination region) functional in plants. In some embodiments, the expression cassette further comprises a nucleotide sequence encoding a nucleic acid which confers resistance to a selection agent (e.g., selectable marker nucleic acid), which allows for the selection for stable transformants. In still further embodiments, expression constructs of the invention may also comprise a leader sequence and/or a sequence allowing for inducible expression of the polynucleotide of interest. See, Guo et al. ((2003) Plant J. 34:383-92) and Chen et al. ((2003) Plant J. 36:731-40) for examples of sequences allowing for inducible expression.

The regulatory sequences of the expression construct are operably linked to the polynucleotide of interest. As used herein, "operably linked", when referring to a first nucleic acid sequence that is operably linked with a second nucleic acid sequence, means a situation when the first nucleic acid sequence is placed in a functional relationship with the second nucleic acid sequence. For instance, a promoter is operably linked to a coding sequence if the promoter effects the transcription or expression of the coding sequence. Generally, operably linked nucleic acid sequences are contiguous and, where necessary to join two protein coding regions, the open reading frames are aligned.

Any promoter capable of driving expression in the plant of interest may be used in the practice of the invention. The promoter may be native or analogous, or foreign or heterologous, to the sugar cane plant into which the expression cassette will be introduced. The terms "heterologous" and "exogenous" when used herein to refer to a nucleic acid sequence (e.g., a DNA or RNA sequence), refer to a sequence that originates from a source foreign to the particular plant (e.g., foreign to the sugar cane plant) or, if from the same source, is modified from its original form. Thus, for example, a heterologous nucleic acid in a sugar cane cell includes a nucleic acid that is endogenous to the particular cell but has been modified through, for example, the use of DNA shuffling. The terms "heterologous" or "exogenous" nucleic acid also includes non-naturally occurring multiple copies of a naturally occurring DNA sequence. Thus, these terms refer to a DNA segment that is foreign or heterologous to the cell, or homologous to the sugar cane cell but in a position within the cell's genome in which the element is not ordinarily found. Exogenous/heterologous DNA segments are expressed to yield exogenous/heterologous polypeptides or functional polynucleotides.

A "homologous" nucleic acid sequence is a nucleic acid (e.g., DNA or RNA) sequence naturally associated with a sugar cane cell into which it is introduced.

The choice of promoters to be included in an expression cassette depends upon several factors, including, but not limited to, efficiency, selectability, inducibility, desired expression level, and cell- or tissue-preferential expression. It is a routine matter for one of skill in the art to modulate the expression of an operably linked sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target sugar cane tissue, but may also lead to some expression in other cell types or tissues as well. Methods for identifying and characterizing promoter regions in plant genomic DNA include, for example, those described in the following references: Jordano et al. (1989) *Plant Cell* 1:855-866; Bustos et al. (1989) *Plant Cell* 1:839-854; Green et al. (1988) *EMBO J.* 7:4035-4044; Meier et al. (1991) *Plant Cell* 3:309-316; and Zhang et al. (1996) *Plant Physiology* 110:1069-1079.

Promoters active in photosynthetic tissue in order to drive transcription in green tissues such as leaves and stems are also contemplated for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc. Natl. Acad. Sci. USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab, rbcS). Other promoters that drive transcription in stems, leaves and green tissue are described in U.S. Patent Publication No. 2007/0006346, herein incorporated by reference in its entirety.

A maize nucleic acid encoding phosphoenol carboxylase (PEPC) has been described in Hudspeth and Grula (1989) *Plant Molec. Biol* 12:579-589. Using standard molecular biological techniques the promoter for this nucleic acid can be used to drive the expression of any nucleic acid in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as gibberellic acid or ethylene, or in response to light or drought.

A variety of transcriptional terminators are available for optional use in expression cassettes. These are responsible for the termination of transcription beyond the coding region of a polynucleotide of interest within the expression cassette and correct mRNA polyadenylation. The termination region may be native with the transcriptional initiation region, may be native with the operably linked DNA sequence of interest, may be native with the sugar cane plant, or may be derived from another source (i.e., foreign or heterologous to the promoter, the DNA sequence of interest, the sugar cane plant, or any combination thereof). Appropriate transcriptional terminators are those that are known to function in plants and include the CAMV 35S terminator, the tml terminator, the nopaline synthase terminator, and the pea rbcs E9 terminator. In addition, the native transcription terminator for any gene may be used.

Numerous sequences have been found to enhance gene expression from within the transcriptional unit and these sequences can be used in conjunction with the expression cassettes of this invention to increase the expression of a polynucleotide of interest in transgenic sugar cane plants and plant parts thereof.

Various intron sequences have been shown to enhance expression, particularly in monocotyledonous cells. Intron 1 of the nucleic acid encoding maize alcohol dehydrogenase was found to be particularly effective and enhanced expression in fusion constructs with the nucleic acid encoding chloramphenicol acetyltransferase (Callis et al. (1987) *Genes Develop.* 1:1183-1200). Intron sequences have been routinely incorporated into plant transformation vectors, typically within the non-translated leader.

A number of non-translated leader sequences derived from viruses are also known to enhance expression, and these are encompassed herein. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (see, for example, Gallie et al. (1987) *Nucleic Acids Res.* 15:8693-8711; Skuzeski et al. (1990) *Plant Molec. Biol.* 15:65-79). Other leader sequences known in the art include, but are not limited to, picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Allison et al. (1986) *Virology* 154:9-20; and Gallie et al. (1995) *Gene* 165:233-238); MDMV leader (Maize Dwarf Mosaic Virus; Allison et al. (1986) *Virology* 154:9-20); human immunoglobulin heavy-chain binding protein (BiP) leader (Macejak and Samow (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV; Gallie et al. (1987) *Nucleic Acids Res.* 15:3257-3273; Gallie et al. (1988) *Nucleic Acids Res.* 16:883-893; Gallie et al. (1992) *Nucleic Acids Res.* 20:4631-4638); and Maize Chlorotic Mottle Virus leader (MCMV; Lommel et al. (1991) *Virology* 81:382-385). See also, Della-Cioppa et al. (1987) *Plant Physiology* 84:965-968.

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins, which is cleaved during chloroplast import to yield the mature protein (see, e.g., Comai et al. (1988) *J. Biol. Chem* 263:15104-15109). These signal sequences can be fused to heterologous gene products to effect the import of heterologous products into the chloroplast (van den Broeck et al. (1985) *Nature* 313:358-363). DNA encoding for appropriate signal sequences can be isolated from the 5' end of the cDNAs encoding the RUBISCO protein, the CAB protein, the EPSP synthase enzyme, the GS2 protein and many other proteins that are known to be chloroplast localized. See also, the section entitled "Expression with Chloroplast Targeting" in Example 37 of U.S. Pat. No. 5,639,949.

The above-described targeting sequences can be utilized not only in conjunction with their endogenous promoters, but also in conjunction with heterologous promoters. Use of promoters that are heterologous to the targeting sequence not only provides the ability to target the sequence but also can provide an expression pattern that is different from that of the promoter from which the targeting signal is originally derived.

In order to ensure the localization in the plastids it is conceivable to use a transit peptide, which includes, but is not limited to, the transit peptide from plastidic Ferredoxin: NADP+ oxidoreductase (FNR) of spinach, which is disclosed in Jansen et al. (1988) Current Genetics 13:517-522. In particular, the sequence ranging from the nucleotides −171 to 165 of the cDNA sequence disclosed therein can be used, which comprises the 5' non-translated region as well as the sequence encoding the transit peptide. Another example of a transit peptide is that of the waxy protein of maize including the first 34 amino acid residues of the mature waxy protein (Klosgen et al. (1989) Mol. Gen. Genet. 217:155-161). It is also possible to use this transit peptide without the first 34 amino acids of the mature protein. Furthermore, the signal peptides of the ribulose bisposphate carboxylase small subunit (Wolter et al. (1988) Proc. Natl, Acad. Sci. USA 85:846-850; Nawrath et al. (1994) Proc. Natl. Acad. Sci. USA 91:12760-12764), of NADP malate dehydrogenase (Galiardo et al. (1995) Planta 197:324-332), of glutathione reductase (Creissen et al. (1995) Plant J. 8:167-(175) and/or of the R1 protein (Lorberth et al. (1998) Nature Biotechnology 16:473-477) can be used.

The nucleic acid of interest to be introduced into a plant tissue or cell thereof of sugar cane using the *Agrobacterium*-mediated transformation methods of the present invention can comprise an expression cassette encoding any polypeptide of interest. Non-limiting examples of polypeptides of interest that are suitable for expression in sugar cane include those resulting in agronomically important traits such as herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. Other non-limiting examples of a polypeptide of interest may also be one that results in increases in plant vigor or yield (including polypeptides that allow a plant to grow at different temperatures, soil conditions and levels of sunlight and precipitation), or one that allows identification of a plant exhibiting a trait of interest (e.g., selectable marker, seed coat color, etc.).

In some embodiments, the transformed sugar cane exhibits resistance to an herbicide. A number of nucleic acids are available, both transgenic and non-transgenic, which confer herbicide resistance. Herbicide resistance is also sometimes referred to as herbicide tolerance. A nucleic acid conferring resistance to an herbicide that inhibits the growing point or meristem, such as an imidazalinone or a sulfonylurea can be suitable. Exemplary nucleic acids in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Nucleic acids conferring resistance to glyphosate are also suitable. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase nucleic acid.

Nucleic acids encoding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561, 236.

Other suitable herbicides include those that inhibit photosynthesis, such as a triazine and a benzonitrile (nitrilase). See, U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are nucleic acids that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Application Publication No. 2001/0016956 and U.S. Pat. No. 6,084,155.

The insecticidal proteins useful for the invention may be expressed in an amount sufficient to control insect pests, i.e., insect controlling amounts. It is recognized that the amount of expression of insecticidal protein in a plant necessary to control insects may vary depending upon the sugar cane cultivar, type of insect, environmental factors and the like. Nucleic acids useful for conferring insect or pest resistance include, for example, nucleic acids encoding toxins identified in *Bacillus* organisms. Nucleic acids encoding *Bacillus thuringiensis* (Bt) toxins from several subspecies have been cloned and recombinant clones have been found to be toxic to lepidopteran, dipteran and coleopteran insect larvae (for example, nucleic acids encoding various delta-endotoxins such as Cry1Aa, Cry1Ab, Cry1Ac, Cry1B, Cry1C, Cry1D, Cry1Ea, Cry1Fa, Cry3A, Cry9A, Cry9C and Cry9B; as well as nucleic acids encoding vegetative insecticial proteins such as Vip1, Vip2 and Vip3). A full list of Bt toxins can be found on the worldwide web at *Bacillus thuringiensis* Toxin Nomenclature Database maintained by the University of Sussex (see also, Crickmore et al. (1998) Microbiol. Mol. Biol. Rev. 62:807-813).

The polypeptide of interest may also be useful for controlling a wide variety of pests including, but not limited to, *Ustilago scitaminea*, sugar cane mosaic virus, *Eldana saccharine, Diatraea saccharalis*, sorghum mosaic virus, etc.

Polypeptides of interest that are suitable for expression in sugar cane further include those that improve or otherwise facilitate the conversion of harvested cane into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the heterologous expression of a cellulase enzyme).

In one embodiment, the polypeptide of interest contributes to improved digestibility for food or feed. Xylanases are hemicellulolytic enzymes that improve the breakdown of plant cell walls, which leads to better utilization of the plant nutrients by the animal. This leads to improved growth rate and feed conversion. Also, the viscosity of the feeds containing xylan can be reduced. Expression of xylanases in plant cells also can also potentially act to facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases," Espoo; Souminen and Reinikainen, eds. (1993) *Foundation for Biotechnical and Industrial Fermentation Research* 8:125-135; U.S. Patent Application Publication No. 2005/0208178; and WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, the polypeptide of interest is a polysaccharide degrading enzyme. Such plants may be useful for generating, for example, fermentation feedstocks for bioprocessing. In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include without limitation: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Further additional enzymes which may be used include proteases, such as fungal and bacterial proteases. Fungal proteases include, for example, those obtained from *Aspergillus, Trichoderma, Mucor and Rhizopus*, such as *A. niger, A. awamori, A. oryzae* and *M miehei*. Of particular interest in the present invention are cellobiohydrolase (CBH) enzymes (EC 3.2.1.91). In one embodiment, the cellobiohydrolase enzyme is CBH1 or CBH2.

Other enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. B.C. 3.1.1.74).

It will also be recognized that the nucleotide sequence encoding the polypeptide of interest may be optimized for increased expression in the transformed sugar cane cell. That is, the nucleotide sequences can be synthesized using sugar cane-preferred codons for improved expression, or may be synthesized using codons at a sugar cane-preferred codon usage frequency. Generally, the GC content of the nucleotide sequence will be increased. See, e.g., Campbell & Gowri (1990) *Plant Physiol.* 92:1-11 for a discussion of host-preferred codon usage. Methods are available in the art for synthesizing plant-preferred genes. See, e.g., U.S. Pat. Nos. 5,380,831, and 5,436,391, and Murray et al. (1989) *Nucleic Acids Res.* 17:477-498, herein incorporated by reference.

After constructing a nucleic acid of interest, for example, one comprising an expression cassette described herein, the construct is incorporated into *Agrobacterium* or other bacteria competent for nucleic acid transfer as described herein and then introduced into a plant, plant part or plant cell by inoculation and co-cultivation in accordance with the transformation methods disclosed herein.

As described above, some embodiments of the present invention lead to regeneration of green plantlets and plants with photosynthetic ability. The test used for confirmation that the nucleotide sequence of interest is stably integrated into the genome of the sugar cane plant depends on the property to be conferred to the plant. For example, when the property is herbicide resistance, confirmation may be achieved by treatment of the growing plants by spraying or painting the leaves with the herbicide in a concentration that is lethal for control plants that have not been subjected to the transformation process.

Where the transferred nucleic acid encodes a polypeptide of interest, expression of that polypeptide in the transformed sugar cane plant can be detected using an immunological method. Immunological methods that can be used include, but are not limited to, competitive and non-competitive assay systems using immune-based techniques such as Western blots, radioimmunoassays, ELISA (enzyme linked immunosorbent assay), multiplex ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and known in the art (see, e.g., *Current Protocols in Molecular Biology*, Vol. 1 (Ausubel et al., eds. John Wiley & Sons, Inc., New York (1994)), which is incorporated by reference herein in its entirety).

In additional embodiments of the present invention, expression can be measured by evaluating patterns of expression of the polynucleotide encoding the polypeptide of interest, or of reporter genes, or both. For example, expression patterns can be evaluated by Northern analysis, polymerase chain reaction (PCR), reverse-transcription PCR (RT-PCR), Taq Man gene expression assay (Applied Biosystems, Inc; Foster City, Calif.), ribonuclease protection assays, fluorescence resonance energy transfer (FRET) detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like. The particular method elected will be dependent on such factors as quantity of RNA recovered, artisan preference, available reagents and equipment, detectors, and the like. Such assays are routine and known in the art (see, e.g., Ausubel et al., supra).

Where the transferred nucleic acid is a functional polynucleotide, the presence and/or efficacy of the polynucleotide in a transformed sugar cane plant can be detected using any suitable method known in the art, including the molecular assays described above. For example, molecular assays that can be used include, but are not limited to, Northern analysis, polymerase chain reaction (PCR), reverse-transcription PCR (RT-PCR), Taq Man gene expression assay (Applied Biosystems, Inc; Foster City, Calif.), ribonuclease protection assays, fluorescence resonance energy transfer (FRET) detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like.

The *Agrobacterium*-mediated transformation methods of the present invention may advantageously reduce the amount of cellular necrosis that normally occurs during co-cultivation of sugar cane plant tissue or cell thereof with, for example, *Agrobacterium*. The methods of the present invention advantageously increase *Agrobacterium*-mediated transformation efficiency in sugar cane when compared to that obtained using the same inoculation and selection protocols, but using a standard co-cultivation protocol, (e.g., wherein the *Agrobacterium*-inoculated plant tissue or cell thereof is co-cultured on a co-cultivation medium), which may be mediated by a reduction in cellular necrosis during co-cultivation. In some embodiments, transformation efficiency is increased by about at least 5%, 10%, 15%, 20%, or 25%. In other embodiments, transformation efficiency is increased by about at least 30%, 35%, 40%, 45%, 50%, or more. Transformation efficiency is calculated as the number of events (e.g., the number of transgenic plants) obtained per gram of starting sugar cane plant tissue.

The present invention will now be described with reference to the following examples. It should be appreciated that this example is for the purpose of illustrating aspects of the present invention, and does not limit the scope of the invention as defined by the claims.

EXAMPLES

Example 1

*Agrobacterium*-Mediated Transformation of Sugar Cane During Desiccation

This example shows that *Agrobacterium*-mediated transformation of sugar cane tissues can be more efficient when performed in desiccating environment.

Methods

Plant Source and Material: Leaf whorl material from field grown sugar cane plants was collected and initiated on EM3 medium (see below). Transverse sections (approximately 20) of immature leaf whorl between 1-3 mm in thickness were taken from just above the meristem and placed in the top-up orientation. Cultures were maintained in the dark at 25° C. for 28 to 42 days. Callus utilized for transformation was within 4-10 days of the last subculture. Callus was selected on morphological characteristics such as compact structure and yellow color. Yellow embryogenic calli were selected wherever possible, as they provided good regeneration, consistent transformation, and fragmented in small clusters (2-4 mm). This was similar among four sugar cane cultivars (e.g., Q208, KQ228, Q117 and Q232).

Preparation of *Agrobacterium*: *Agrobacterium* cultures harboring a vector comprising green fluorescent protein (GFP; GFP is an exemplary scorable marker that allows determination of gene delivery efficiency using a fluorescent microscope) or nptII (selectable marker) were streaked out on LB medium (see below) containing appropriate antibiotics and grown at 28° C. for 3 days and then stored at 4° C. for up to 1 month. Prior to transformation, a single colony was selected and streaked onto a fresh LB plate and grown for 1-2 days at 28° C.

An *Agrobacterium* culture was initiated in 30 ml of AB medium (see below) or LB medium from an isolated colony and grown for 4-5 hours at 28° C. in a shaker at 200 revolutions per minute (RPM). The culture was transferred to a 500 ml Erlenmeyer flask with 100-150 ml of fresh AB or LB medium. The culture grown for 12-14 hours in 28° C. with 150 RPM to an optical density (OD) of 0.2-1.0 at 600 nm.

The *Agrobacterium* culture was then centrifuged for 20 minutes at 2000 RPM at 25° C. The pellet obtained was resuspended in 150 ml ½ strength Murashige & Skoog (MS) medium (without sucrose) supplemented with 400 µM of acetosyringone. This culture was then maintained at 28° C. at 150 RPM for 4 hours prior to infection. OD was adjusted to a desired level before infection of the plant material to be transformed.

Infection and co-cultivation: Callus tissue was weighed to ensure all experiments could be compared. Approximately 10 g of callus tissue was used per treatment and was placed into a 200 ml culture vessel. Callus tissue was heat shocked (not done for Q208) at 45° C. for 5 minutes by adding 50 ml of pre-warmed ½ strength MS (without sucrose) medium and then maintaining the callus in a water bath at 45° C. MS medium was then drained from the callus tissue, and 25 ml of the *Agrobacterium* inoculation suspension was added to each vessel and mixed gently. The callus/*Agrobacterium* mixture was vacuum-infiltrated by placing it into a vacuum chamber for 10 minutes at −27.5 mmHg of vacuum. The callus/*Agrobacterium* mixture was then rested for 5-10 minutes in the dark.

The *Agrobacterium* inoculation suspension was then drained from the callus, and the remaining callus culture was blotted dry to remove excess *Agrobacterium* inoculation suspension. Plant tissues were blotted on filter paper such as Whatman Grade 1 paper, until the *Agrobacterium* inoculation suspension was substantially removed. The callus was then transferred for co-cultivation to 90×25-mm petri dishes containing no co-culture medium or containing dry filter papers or filter papers wet with sterile water, and sealed with NESCOFILM®, MICROPORE™ tape (3M; Minneapolis, Minn.) or similar material. Controls were cocultivated on media as control treatments. Some additional treatments with pre or post co-cultivation desiccation were also included as described in the table below. The dishes were incubated in the dark at 22° C. for 2-3 days.

Post-transformation: After co-cultivation, the callus tissue was transferred to MS 1 medium (see below) containing with 200 mg/L of timentin ("resting" medium) and kept in the dark at 25° C. for 4 days. The first selection step was made in MS 2 medium (see below) containing 50 mg/L of geneticin and 200 mg/L of timentin for 14-15 days in the dark at 25° C.

Regeneration and rooting: Regeneration was conducted on MS 3 medium (see below) supplemented with 50 mg/L of geneticin and 200 mg/L of timentin at 25° C. in 16 hr light. Gradual increases in light intensity were required. For the first week, the culture was left on a laboratory bench under normal room lighting, and for the next 3 weeks, the culture was grown at moderate light intensity.

Shoot formation was seen between 2-4 weeks. When the first leaves appeared, the shoots were transferred to MS 4 medium (see below) until the plants grew to 4-5 cm in height. They were then sampled for analysis and transferred to soil.

Media: The components within the media referred to above are as follows.

EM3: MS salts and vitamins; 0.5 g/L casein hydrolysate; 100 ml/L coconut water; 20 g/L sucrose and 3 mg/1 2,4-D.

LB basic: 10 g/L NaCl; 5 g/L yeast extract; and 10 g/L tryptone.

LB solid: LB basic with 15 g/L of agar.

AB: The following salts were autoclaved and added: 2 g/L $(NH_4)_2SO_4$; 6 g/L $Na_2HPO_4$; 3 g/L $KH_2PO_4$; and 3 g/L NaCl. The following compounds were filter sterilized: 0.1 mM $CaCl_2$; 1.0 mM $MgCl_2$; 0.003 mM $FeCl_3$; and 5 g/L glucose.

MS basic: MS medium salts and vitamins, with 25 g/L sucrose.

MS 1: MS basic supplemented with 3.0 mg/L 2,4-D and 200 mg/L Timentin.

MS 2: MS basic supplemented with 3.0 mg/L 2,4-D and 50 mg/L Geneticin and 200 mg/L Timentin.

MS 3: MS basic supplemented with 40 ml of coconut water filter sterilized and 1.0-2.0 mg/L BAP (cultivar dependent, thus not required for all cultivars) and 50 mg/L Geneticin and 200 mg/L Timentin.

MS 4: MS basic supplemented with 1.0 g/L charcoal and 1.0 mg IBA (indole-3-butyric acid, not required for all cultivars and 50 mg/L Geneticin.

CoCult: Media co-cultivation media as described for banana in Khanna et al. *Molecular Breeding* 14(3): 239-252 (2004).

As shown in the tables below, six different co-cultivation conditions were studied for the Q117 sugar cane cultivar. The co-cultivation conditions varied from no co-culture medium (i.e., no medium), in which the plant tissues were cultured on the bottom of the plate only, with dry filter paper, or with wet filter paper. The transformation vectors were either pUGfpN(s) or pUbiNptII(s).

The transformation vector pUGFPN(s) contains two expression cassettes between the left and right border of the transformation vector. One of the expression cassettes contains the following elements operably linked together: maize ubiquitin promoter linked to a nucleic acid sequence encoding green fluorescent protein, followed by the S65 termination sequence. The second expression cassette contains maize ubiquitin promoter linked to a nucleic acid sequence encoding the protein NptII which confers geneticin resistance, followed by the Nos terminator sequence. The transformation vector pUbiNptII(s) contains an expression cassette between the left and right borders of the transformation vector. This expression cassette contains the following elements operably linked together: maize ubiquitin promoter linked to a nucleic acid sequence encoding the protein NptII which confers geneticin resistance, followed by the Nos terminator sequence.

TABLE 1

Summary of the six co-cultivation conditions with Q117 callus. Weight change over co-cultivation period, number of transgenic events obtained and GFP sector development at 22 days is also shown.

| Condition | Construct | OD | Initial Callus Mass (g) | Co-Cultivation Condition | Weight after co-cultivation[1] | |
|---|---|---|---|---|---|---|
| | | | | | | Transgenic Events obtained |
| 1 | pUbiNpt II(s) | 0.7 | 20 | No medium | 14.2 (−29%) | 118 |
| 2 | pUbiNpt II(s) | 0.7 | 20 | MS medium + 3% sucrose | 30.4 (+52%) | 0 |
| 3 | pUbiNpt II(s) | 0.7 | 20 | CoCult medium | 24.8 (+24%) | 1 |
| 4 | pUbiNpt II(s) | 0.7 | 20 | Filter paper alone | 13.9 (−30%) | 128 |
| 5 | pUbiNpt II(s) | 0.7 | 20 | Filter paper + 0.5 ml $H_2O$ | 14.4 (−28%) | 80 |
| 6 | pUbiNpt II(s) | 0.7 | 20 | Filter paper + 1 ml $H_2O$ | 16.1 (−20%) | 38 |
| | | | | | | GFP Sectors (22 days) |
| 7 | pUGfpN(s) | 0.7 | 7.2 | No medium | 5.5 (−24%) | 20 |
| 8 | pUGfpN(s) | 0.7 | 7.2 | MS medium + 3% sucrose | 8.5 (+18%) | 0 |
| 9 | pUGfpN(s) | 0.7 | 7.2 | CoCult medium | 10.1 (+40%) | 1 |
| 10 | pUGfpN(s) | 0.7 | 7.2 | Filter paper alone | 5.0 (−31%) | 35 |
| 11 | pUGfpN(s) | 0.7 | 7.2 | Filter paper + 0.5 ml $H_2O$ | 5.2 (−28%) | 19 |
| 12 | pUGfpN(s) | 0.7 | 7.2 | Filter paper + 1 ml $H_2O$ | 5.5 (−24%) | 13 |

[1]Change in weight over co-cultivation compared to starting weight is indicated in parentheses.

As shown in Table 1, expression of the nucleic acid encoding the GFP scorable marker, and transgenic event recovery (thus, transformation efficiency), was highest in those plant tissues where culturing during the co-cultivation step occurred on the more extreme desiccating environments, i.e., a plate surface alone or on dry filter paper as compared to those treatments with no desiccation (i.e. treatments 2, 3, 8, and 9).

A duplicate study was performed with a different sugar cane cultivar (Q208) as shown in Table 2. Leaf whorl material from field grown sugar cane plants was collected and initiated on EM3 medium.

meristem up to 2-3 cm above. The isolated leaf rolls were cultured on SC+0.75 mg-3 mg/L 2,4-D medium (2-10/plate) in the dark at 28° C. for 2-3 weeks. High quality embryogenic culture responses were then selectively sub-cultured to fresh SC+D medium to serve as target material for transformation.

Transformation vector and *Agrobacterium* strains: Binary vectors in an *A. tumefaciens* strain such as LB4404 or EHA101 were used for sugar cane transformation. Depending on the construct, the binary vector harbors either the Reef Coral green fluorescent protein (GFP; for construct pNOV2145) or the Reef Coral Cyano-Fluorescent protein (CFP; for construct 13601) as a scorable marker nucleic acid.

TABLE 2

Summary of the six co-cultivation conditions with Q208 callus. Weight change over co-cultivation period, number of transgenic events obtained and GFP sector development at 22 days is also shown.

| Condition | Construct | OD | Initial Callus Mass (g) | Co-Cultivation Condition | Weight after co-cultivation[1] | Transgenic Events obtained |
|---|---|---|---|---|---|---|
| 1 | pUbiNptII(s) | 1.0 | 20 | No medium | 17.5 (−13%) | 0 |
| 2 | pUbiNptII(s) | 1.0 | 20 | MS medium + 3% sucrose | 32.9 (+64%) | 0 |
| 3 | pUbiNptII(s) | 1.0 | 20 | CoCult medium | 28.6 (+43%) | 0 |
| 4 | pUbiNptII(s) | 1.0 | 20 | Filter paper alone | 16.3 (−19%) | 0 |
| 5 | pUbiNptII(s) | 1.0 | 20 | Filter paper + 0.5 ml $H_2O$ | 16.8 (−16%) | 0 |
| 6 | pUbiNptII(s) | 1.0 | 20 | Filter paper + 1 ml $H_2O$ | 17.5 (−13%) | 1 |
|   |   |   |   |   |   | GFP Sectors (22 days) |
| 7 | pUGfpN(s) | 1.0 | 10 | No medium | 9.0 (−10%) | 13 |
| 8 | pUGfpN(s) | 1.0 | 10 | MS medium + 3% sucrose | 14.8 (+48%) | 0 |
| 10 | pUGfpN(s) | 1.0 | 10 | Filter paper alone | 7.5 (−25%) | 9 |
| 11 | pUGfpN(s) | 1.0 | 10 | Filter paper + 0.5 ml $H_2O$ | 8.4 (−16%) | 20 |
| 12 | pUGfpN(s) | 1.0 | 10 | Filter paper + 1 ml $H_2O$ | 9.0 (−10%) | 14 |

[1]Change in weight over co-cultivation compared to starting weight is indicated in parentheses.

Example 2

Further Protocol for *Agrobacterium*-Mediated Transformation of Sugar Cane During Desiccation This example shows further methods of transforming sugar cane cells and tissue in a desiccating environment. This example uses tillers as the starting source of plant tissue.

Plant source and material: Embryogenic callus was obtained from sugar cane (*Saccharum* hybrid) stock plants grown in the greenhouse.

Induction of embryogenic callus: Immature tillers were collected at the development stage where the lower internode is beginning to elongate. The immature tillers were sterilized by either spraying with 70% ethanol or immersing in 20% CLOROX® Bleach (The Clorox Company; Oakland, Calif.) (with 3 drops of TWEEN®-20/L; Sigma Aldrich; St. Louis, Mo.) for 20 minutes, and then rinsed 3 times with sterile tap water.

Leaf rolls were then isolated from sterilized tillers, by cutting 1-2 mm transverse sections from just above the apical

*Agrobacterium* cultures were initiated weekly from −80° C. freezer glycerol stock onto YP plate containing appropriate antibiotics and grown at 28° C. in an incubator as follows.

*Agrobacterium* strains were removed from the −80° C. freezer and placed on dry ice. Bacterial growth media was taken from 4° C. storage with appropriate antibiotics for each of the *Agrobacterium* strains (usually, YP/Spec, Kan).

A small amount of the *Agrobacterium* strain from the vial was removed with a sterile disposable plastic inoculating loop and placed on the plate. *Agrobacterium* was spread with a loop or cell spreader, to create a thin layer of cells over the surface of the growth medium.

Plates were placed in an incubator at 28° C. for about 2 days prior to use. One colony was cultured overnight in YP liquid media with appropriate antibiotics. *Agrobacterium* cells were then centrifuged at 5000 rpm for 10 minutes at room temperature. The supernatant was removed, and a cell pellet was re-suspended in liquid inoculation medium such as SCInoc (see below). Light absorption of the bacterial suspension was measured in a spectrophotometer and diluted to $A_{660}$ of 0.1-0.85. Acetosyringone was added to a final concentration of 40-80 mg/L (200-400 μM) to induce virulence gene expression for 10 minutes up to 4 hours.

Preparation of Plant Tissue: Embryogenic callus and leaf rolls were used for transformation. The best quality target pieces were visually selected from the embryogenic culture lines for use in transformation. Leaf rolls cultured on callus induction medium SC2D (see below) for 1, 3, 5, and up to 30 days were used for transformation.

Infection and Co-cultivation of Sugar Cane Plant Tissue: The prepared explants were pretreated with heat shock at 45° C. as described in Example 1 for 5 minutes. The heat shock liquid was removed, and the plant tissue was mixed with the *Agrobacterium* suspension. The mixture was incubated for at least 1 minute or up to overnight at room temperature.

*Agrobacterium* suspension culture was drained from the explants and excess suspension culture was removed by blotting with sterilized filter paper or air drying for 10-60 minutes or both.

The pre-dried explants were placed in an empty plate with or without a filter paper (supplemented with 50-1000 μl infection media, e.g., SCInoc (see below)). The co-cultivation plates were then incubated for 3 to 5 days at 20° C.-28° C. in the dark. A control co-cultivation treatment with SCCoCult medium (see below) was carried out.

Resting stage: The infected plant parts were transferred to a resting medium for 2-10 days to facilitate recovery of transgenic material. A recovery medium without selection agent, such as SCRecov (see below) with appropriate antibiotics to inhibit *Agrobacterium* growth is used during the resting stage.

Selection and regeneration of transgenic plants: After the resting stage (i.e., recovery period), the explants were transferred to selection medium such as SCSe1 or SCMan (see below) and then cultured at 28° C. in the dark for 3-6 weeks.

Proliferating sectors were selectively sub-cultured to regeneration media such as SCManRegen (with appropriate antibiotics) (see below) for regeneration induction and then cultured at 28° C. in the dark for 1 week. After 1 week, the regeneration induction plates were cultured in the light at 28° C. for 16 hours/day. After 2 weeks, developing shoots were transferred to sugar cane rooting media (SCR, see below) for shoot elongation and rooting.

Media compounds: The components within the media referred to above are as follows.

| Name of Chemical | Amount | Units |
|---|---|---|
| Recipe Name SC2D Final pH 5.8 Recipe for 1 L | | |
| MS Basal Salt Mixture | 4.3 | g |
| B5 Vitamins 200X | 5 | ml |
| Sucrose | 30 | g |
| 2,4-D 1 mg/ml | 2 | ml |
| Phytablend | 7 | g |
| Recipe Name SCInoc Final pH 5.3 Recipe for 1 L | | |
| MS Basal Salt Mixture | 4.3 | g |
| B5 Vitamins 200X | 5 | ml |
| Sucrose | 88.5 | g |
| Glutamine 50 mg/ml | 17.5 | ml |
| Glucose | 36 | g |
| 2,4-D 1 mg/ml | 1 | ml |
| Arginine | 174 | mg |
| Glycine 1 mg/ml | 7.5 | ml |
| Aspartic Acid | 266 | mg |
| Casein Hydrolysate Enzymatic | 500 | mg |
| Acetosyringone 40 mg/ml | 1 | ml |
| Recipe Name SCCoCult Final pH 5.3 Recipe for 1 L | | |
| MS Basal Salt Mixture | 4.3 | g |
| B5 Vitamins 200X | 5 | ml |
| Sucrose | 30 | g |
| Glutamine 50 mg/ml | 17.5 | ml |
| Glucose | 30 | g |
| 2,4-D 1 mg/ml | 1 | ml |
| Arginine | 174 | mg |
| Glycine 1 mg/ml | 7.5 | ml |
| Phytagel | 3 | g |
| Aspartic Acid | 266 | mg |
| Casein Hydrolysate Enzymatic | 500 | mg |
| Recipe Name SCRecov Final pH 5.8 Recipe for 1 L | | |
| MS Basal Salt Mixture | 4.3 | g |
| B5 Vitamins 200X | 5 | ml |
| Sucrose | 30 | g |
| 2,4-D 1 mg/ml | 2 | ml |
| Phytablend | 7 | g |
| Ticarcillin potassium clavulanate 15:1 100 mg/ml | 2.5 | ml |
| Recipe Name SCMan Final pH 5.8 Recipe for 1 L | | |
| MS Basal Salt Mixture | 4.3 | g |
| B5 Vitamins 200X | 5 | ml |
| Sucrose | 20 | g |
| 2,4-D 1 mg/ml | 2 | ml |
| Phytablend | 7 | g |
| Mannose 1 g/ml | 3 | ml |
| Ticarcillin potassium clavulanate 15:1 100 mg/ml | 2.5 | ml |
| Recipe Name SCManRege Final pH 5.8 Recipe for 1 L | | |
| MS Basal Salt Mixture | 4.3 | g |
| B5 Vitamins 200X | 5 | ml |
| Sucrose | 24 | g |
| BA 1 mg/ml | 2 | ml |
| Phytablend | 7 | g |
| Mannose 1 g/ml | 3 | ml |
| Recipe Name SCR Final pH 5.8 Recipe for 1 L | | |
| MS Basal Salt Mixture | 4.3 | g |
| B5 Vitamins 200X | 5 | ml |
| Sucrose | 20 | g |
| Phytablend | 7.0 | g |
| NAA 1 mg/ml | 0.5 | ml |

As shown in Table 3 below, three different co-cultivation conditions were studied. The co-cultivation conditions varied culturing with co-culture medium, no co-culture medium (i.e., no medium), in which case the explants were cultured on the bottom of the plate, to wet filter paper. Transient GFP (construct pNOV2145) or CFP (construct 13601) expression, and thus transformation efficiency, was highest in those plant tissues cultured on the plate surface alone or on wet filter paper.

TABLE 3

Summary of the three co-cultivation conditions.

| Cultivar | Strain and Construct | Co-cultivation Treatment[1,3] | Transient Expression[2] | Stable callus lines |
|---|---|---|---|---|
| CP84-1198 | EHA101 (pNOV2145) | Co-culture medium | * | N/A[4] |
| | | Filter | *** | N/A |
| | | No medium | *** | N/A |
| TCP72-1210 | EHA101 (pNOV2145) | Co-culture medium | * | N/A |
| | | Filter | *** | N/A |
| | | No medium | *** | N/A |
| L-99-226 | EHA101 (pNOV2145) | Co-culture medium | * | N/A |
| | | Filter | *** | N/A |
| | | No medium | *** | N/A |
| L-97-128 | EHA101 (pNOV2145) | Co-culture medium | * | N/A |
| | | Filter | *** | N/A |
| CP84-1198 | EHA101 (pNOV2145) | Co-culture medium | * | 1 |
| | | Filter | *** | 3 |
| CP-84-1198 | EHA101 (13601) | Co-culture medium | ** | 11 |
| | | Filter | ***** | 31 |
| L 97-128 | EHA101 (pNOV2145) | Co-culture medium | * | 1 |
| | | Filter | ***** | 8 |

[1]Co-culture medium was used during co-cultivation stage; "Filter" represents only wet filter paper was used during co-cultivation; "No medium" represents explants were co-cultivated on an empty plate without any medium or filter paper.
[2]More * indicates higher transient expression
[3]Equal amount of explants were used for the different treatments
[4]N/A = data not available or not collected

Example 3

*Agrobacterium*-Mediated Transformation of Sugar Cane During Extended Desiccation This example shows that the methods described above can be carried out for an extended length of time.

Methods

The methods of Example 1 were repeated; however, the co-cultivation period is extended by a few days to nearly one week to alter the rate and extent of desiccation. Briefly, five different co-cultivation conditions were carried out for three or five days. In the first co-cultivation condition, callus tissue was kept for one hour on a filter paper and then co-cultivated for three days without medium. In the second co-cultivation condition, callus tissue was co-cultivated on a filter paper for three days. In the third co-cultivation condition, callus tissue was treated as in the second condition but included 500 μl H$_2$O placed on the filter paper. In the fourth co-cultivation tissue, callus tissue was treated as in the second condition but included 1000 μl H$_2$O placed on the filter paper. In the fifth co-cultivation condition, callus tissue was treated as in the first condition but co-cultivated for five days.

As shown in Tables 4 and 5, GFP expression levels and number of events generated were relatively unaffected by an increase in co-cultivation time but indicates that a longer co-cultivation period of up to 9 days still results in a useful number of transformation events

TABLE 4

Summary of GFP expression under various co-cultivation conditions. 10 g of callus was used for each transformation condition.

| Condition | Treatment | GFP Sectors (22 Days) |
|---|---|---|
| 1 | No medium for 3 days co-cultivation | 39 |
| 2 | One filter paper | 49 |
| 3 | Filter paper + 500 μl H$_2$O | 34 |
| 4 | Filter paper + 1000 μl H$_2$O | 26 |
| 5 | No medium for 5 days co-cultivation | 34 |

TABLE 5

Summary of transgenic event generation following various co-cultivation time conditions. 20 g of callus was used for each transformation condition.

| Condition | Treatment | Number of transgenic events/gram of original callus |
|---|---|---|
| 1 | No medium for 3 days co-cultivation | 0.95 |
| 2 | No medium for 5 days co-cultivation | 0.4 |
| 3 | No medium for 7 days co-cultivation | 0.4 |
| 4 | No medium for 9 days co-cultivation | 0.5 |
| 5 | No drying prior to co-cultivation with no medium for 3 days | 0.15 |

Example 4

Comparison of *Agrobacterium*-Mediated Transformation of Sugar Cane During Desiccation at Varied Time Points This example shows the effects of post-infection drying and post-co-cultivation drying of the sugar cane cells and tissue.

Briefly, the methods of Example 1 were repeated; however, a pre- or post-co-cultivation drying was applied to some cultures to alter the rate and extent of desiccation.

When combined with traditional co-cultivation (on media) or desiccation co-cultivation (as described herein), neither a pre-infection nor post-co-cultivation drying step improved the methods of Example 1 or Example 2. As shown in Table 6, GFP sector development decreased in cultures that were subjected to a pre- or post-infection drying. Each culture had a starting weight of 10 g of callus.

TABLE 6

Summary of GFP expression under various co-cultivation conditions.

| Condition | Treatment | Wt after Co-cultivation[1] | GFP Sectors (22 days) |
|---|---|---|---|
| 1 | 30 minute pre-infection drying, followed by co-cultivation in MS semi-solid medium | 14.9 (+49%) | 0 |
| 2 | 30 minute pre-infection drying, followed by co-cultivation on filter paper with no medium | 7.6 (−24%) | 16 |
| 3 | 30 minute pre-infection drying, followed by co-cultivation with no medium | 7.9 (−21%) | 20 |
| 4 | Callus dried on one filter paper for 1 hour, followed by co-cultivation with no medium | 7.8 (−22%) | 14 |
| 5 | Co-cultivation on one filter paper with no medium | 6.8 (−32%) | 16 |
| 6 | Co-cultivation on one filter paper with 500 μl H$_2$O | 6.4 (−36%) | 53 |

TABLE 6-continued

Summary of GFP expression under various co-cultivation conditions.

| Condition | Treatment | Wt after Co-cultivation[1] | GFP Sectors (22 days) |
|---|---|---|---|
| 7 | Co-cultivation on one filter paper with 1000 µl H$_2$O | 6.6 (−34%) | 54 |
| 8 | Co-cultivation on two filter papers with no medium | 6.9 (−31%) | 30 |
| 9 | Co-cultivation on one filter paper changed daily | 6.5 (−35%) | 10 |
| 10 | Co-cultivation on one filter paper with no medium followed by 30 minute post-co-cultivation drying | 5.9 (−41%) | 23 |
| 11 | Co-cultivation on one filter paper with no medium followed by 60 minutes post-co-cultivation drying | 5 (−50%) | 6 |
| 12 | Co-cultivation on MS solid medium | 14.7 (+47%) | 0 |

[1]Change in weight over co-cultivation compared to starting weight is indicated in parentheses; each culture had a starting weight of 10 g of callus.

Similarly, when combined with traditional co-cultivation (on media) or desiccation co-cultivation (as described herein), neither a pre-infection nor a post-co-cultivation drying step improved the methods of Example 1 or Example 2. As shown in Table 7, stable transgenic event production after transformation with nptII vector decreased in cultures that were subjected to a pre-infection or post-co-cultivation drying. Each culture had a starting weight of 10 g of callus.

TABLE 7

Summary of transgenic event generation efficiency following various co-cultivation conditions.

| Condition | Treatment | Wt after Co-cultivation[1] | Number of transgenic events generated. |
|---|---|---|---|
| 1 | 30 minute pre-infection drying, followed by co-cultivation in MS semi-solid medium | 12.5 (+25%) | 2 |
| 2 | 30 minute pre-infection drying, followed by co-cultivation on filter paper with no medium | 6.9 (−21%) | 17 |
| 3 | 30 minute pre-infection drying, followed by co-cultivation with no medium | 6.9 (−21%) | 17 |
| 4 | Callus dried on one filter paper for 1 hour, followed by co-cultivation with no medium | 6.7 (−33%) | 33 |
| 5 | Co-cultivation on one filter paper with no medium | 6.3 (−37%) | 24 |
| 6 | Co-cultivation on one filter paper with 500 µl H$_2$O | 6.4 (−36%) | 19 |
| 7 | Co-cultivation on one filter paper with 1000 µl H$_2$O | 6.6 (−34%) | 19 |
| 8 | Co-cultivation on two filter papers with no medium | 6.9 (−31%) | 21 |
| 9 | Co-cultivation on one filter paper changed daily | 6.2 (−38%) | 31 |
| 10 | Co-cultivation on one filter paper with no medium followed by 30 minute post-co-cultivation drying | 5.6 (−44%) | 15 |
| 11 | Co-cultivation on one filter paper with no medium followed by 60 minutes post-co-cultivation drying | 4.2 (−58%) | 7 |
| 12 | Co-cultivation on MS solid medium | 14.1 (+41%) | 2 |

[1]Change in weight over co-cultivation compared to starting weight is indicated in parentheses; each culture had a starting weight of 10 g of callus.

The foregoing examples demonstrate that sugar cane can be efficiently transformed by subjecting the *Agrobacterium*-inoculated plant tissue to extreme desiccation during the co-cultivation step, in which plant tissues can lose weight over an extended period of time. By culturing the *Agrobacterium*-inoculated plant tissue in the desiccating environment during the co-cultivation step, transformation efficiency was increased.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A method of producing a transformed sugar cane tissue or cell thereof, said method comprising:
   a) inoculating a sugar cane tissue or a cell thereof with an *Agrobacterium* inoculation suspension, said *Agrobacterium* comprising a nucleic acid of interest, to obtain an *Agrobacterium*-inoculated sugar cane tissue or cell thereof; and
   b) co-cultivating said *Agrobacterium*-inoculated sugar cane tissue or cell thereof on a surface in the absence of co-culture media and in a desiccating environment for a time period sufficient to reduce original weight of said *Agrobacterium*-inoculated sugar cane tissue or cell thereof by at least 35%, thereby producing a transformed sugar cane tissue or cell thereof.

2. The method of claim 1, wherein said co-cultivating comprises culturing said *Agrobacterium*-inoculated sugar cane tissue or cell thereof on at least one layer of dry paper.

3. The method of claim 2, wherein said co-cultivating comprises culturing said *Agrobacterium*-inoculated sugar cane tissue or cell thereof on two or more layers of dry paper.

4. The method of claim 2, further comprising changing the paper periodically during co-cultivation.

5. The method of claim 3, further comprising changing the paper periodically during co-cultivation.

6. The method of claim 4, further comprising changing the paper each day during the co-cultivation.

7. The method of claim 5, further comprising changing the paper each day during the co-cultivation.

8. The method of claim 1, wherein said inoculation suspension is substantially removed from said *Agrobacterium*-inoculated sugar cane tissue or cell thereof prior to co-cultivating in the absence of co-cultivation media.

9. The method of claim 1, wherein said co-cultivating comprises culturing said *Agrobacterium*-inoculated sugar cane tissue or cell thereof on said surface in the absence of dry paper.

10. The method of claim 1, further comprising selecting a transformed sugar cane tissue or cell thereof comprising the nucleic acid of interest, wherein said nucleic acid of interest comprises an expression cassette comprising a nucleic acid that confers resistance to a selection agent, and wherein said selecting comprises culturing said *Agrobacterium*-inoculated sugar cane tissue or cell thereof in a medium comprising said selection agent, and selecting a transformed sugar cane tissue or cell thereof comprising said nucleic acid of interest.

11. The method of claim 1, wherein said sugar cane tissue or cell thereof is obtained from a sugar cane stalk or tiller.

12. The method of claim 1, wherein said sugar cane tissue or cell thereof is embryogenic callus tissue.

13. The method of claim 11, wherein said sugar cane tissue or cell thereof is obtained from a leaf roll segment or a leaf sheath segment excised from said stalk or tiller.

14. The method of claim 11, wherein said sugar cane tissue or cell thereof is obtained by pre-culturing a segment of said stalk or tiller for a period of time to produce embryogenic callus tissue prior to contacting said sugar cane tissue or cell thereof with said inoculation suspension comprising *Agrobacterium*.

\* \* \* \* \*